(12) United States Patent
Cumming

(10) Patent No.: US 6,716,847 B2
(45) Date of Patent: Apr. 6, 2004

(54) SUBSTITUTED ANILINO-QUINOLINE COMPOUNDS AND USE THEREOF

(75) Inventor: John G Cumming, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/441,084

(22) Filed: May 20, 2003

(65) Prior Publication Data

US 2003/0216417 A1 Nov. 20, 2003

Related U.S. Application Data

(62) Division of application No. 09/787,883, filed as application No. PCT/GB99/03220 on Sep. 27, 1999, now Pat. No. 6,593,333.

(30) Foreign Application Priority Data

Oct. 1, 1998 (GB) ............................................. 9821338
Mar. 23, 1999 (GB) ............................................. 9906564

(51) Int. Cl.$^7$ ........................ A61K 31/47; C07D 215/42
(52) U.S. Cl. .................................. 514/253.06; 546/160
(58) Field of Search ...................... 546/160; 514/253.06

(56) References Cited

U.S. PATENT DOCUMENTS

| | | | |
|---|---|---|---|
| 1,903,899 | A | 4/1933 | Laska et al. |
| 1,909,960 | A | 5/1933 | Hitch |
| 3,211,555 | A | 10/1965 | Mory et al. |
| 3,755,332 | A | 8/1973 | Wasley et al. |
| 4,367,328 | A | 1/1983 | Bertram et al. |
| 4,524,168 | A | 6/1985 | Wick |
| 4,749,729 | A | 6/1988 | Kohli et al. |
| 6,127,374 | A | 10/2000 | Bridges |
| 2002/0169165 | A1 | 11/2002 | Kath et al. |
| 2003/0018029 | A1 | 1/2003 | Barker et al. |

FOREIGN PATENT DOCUMENTS

| | | |
|---|---|---|
| DE | 28 12 252 | 10/1979 |
| EP | 0 566 226 | 10/1993 |
| EP | 0 635 507 | 1/1995 |
| EP | 0 849 256 A1 | 6/1998 |
| EP | 0 945 443 | 9/1999 |
| GB | 522 788 | 3/1931 |
| JP | 61-204221 | 9/1986 |
| WO | 93/04170 | 3/1993 |
| WO | 95/19774 | 7/1995 |
| WO | 95/35304 | 12/1995 |
| WO | 97/05878 | 2/1997 |
| WO | 97/13771 | 4/1997 |
| WO | 97/32853 | 9/1997 |
| WO | 97/33883 | 9/1997 |
| WO | 98/06715 | 2/1998 |
| WO | 98/22103 | 5/1998 |
| WO | 99/01439 | 1/1999 |
| WO | 00/12485 | 3/2000 |
| WO | 00/12486 | 3/2000 |
| WO | 00/12487 | 3/2000 |

OTHER PUBLICATIONS

Adams et al., "Search for trypanocides. III. Analogs of suramin.", Chemical Abstracts, vol. 51, 1957, columns 5068 and 5069.
Ando et al., "Producing azo lake pigments"; Chemical Abstract, vol. 106, Abstract No, 215574.
Ando et al., "Substituent Shielding Parameters of Ffluorine–19 NMR on Polyfluoroaromatic Compounds Dissolved in Dimethyl Sulfoxide–$d_6$", Magn. Reson.Chem. 639–45, 1995, Chemical Abstract: 123: 227514, 1995.
Ashton et al., "New Low–Density Lipoprotein Receptor Upregulators Acting via a Novel Mechanism", J. Med. Chem., 1996, vol. 39, pp. 3343–3356.
Beilstein Reg. No. 2164595, no date given.
Beilstein Reg. No. 3166971, no date given.
Beilstein Reg. No. 3451759, no date given.
Beilstein Reg. No. 3480574, no date given.
Beilstein Reg. No. 3483669, no date given.
Beilstein Reg. No. 3534091, no date given.
Beohm et al., "New inhibitors of p38 kinase", Exp. Opin. Ther. Patents, 10(1), 2000, pp. 25–37.
Chemical Abstract No. 12076g, vol. 65, 1966.
Chemical Abstract No. 12932a, vol. 51, 1957.
Denny et al., "Potential Antitumour Agents. 29. Quantitative Structure–Activity Relationships for the Antileukemic Bisquaternary Ammonium Heterocycles", Journal of Medicinal Chemistry, Feb. 1979, vol. 22, No. 2, pp. 134–150.
English et al., "Pharmacological inhibitors of MAPK pathways", Trends Pharmac. Sci. 23, 2002, pp. 40–45.
Hamuro et al., "Novel Folding Patterns in a Family of Oligoanthranilamides: . . . Secondary Structures", J. Amer. Chem. Soc., 1997, pp. 10587–10593.
Hanson, "Review—Pulmonary–Allergy, Dermatological, Gastrointestinal & Arthritis—Inhibitors of p38 kinase", Exp. Opin. Ther. Patents, 1997, XP–002086152, pp. 729–733.
Ito et al., Photosensitive material containing microencapsulated hydrazine derivatives; Chemical Abstract, vol. 118, Abstract No. 70021.

(List continued on next page.)

Primary Examiner—Zinna Northington Davis
(74) Attorney, Agent, or Firm—Morgan, Lewis & Bockius LLP

(57) ABSTRACT

The invention concerns amide derivatives of Formula (I), wherein: G is N or CH; $R^1$ is a group such as hydroxy, halo, trifluoromethyl, $C_{1-6}$alkyl and $C_{1-6}$alkoxy; each of $R^2$ and $R^3$ is hydrogen, halo, $C_{1-6}$alkyl, $C_{2-6}$alkenyl or $C_{2-6}$alkynyl; $R^4$ is a group such as hydrogen, hydroxy, $C_{1-6}$alkyl, $C_{1-6}$alkoxy and $C_{3-7}$cycloalkyl, or $R^4$ is of the Formula (IC): —K-J, wherein J is aryl, heteroaryl or heterocyclyl and K is a bond or a group such as oxy and imino, $R^5$ is a group such as hydrogen, halo and trifluoromethyl; m is 1–3 and q is 0–4; or pharmaceutically acceptable salts or in vivo cleavable esters thereof; processes for their preparation, pharmaceutical compositions containing them and their use in the treatment of diseases or medical conditions mediated by cytokines.

9 Claims, No Drawings

OTHER PUBLICATIONS

Kelley et al., "Antirhinovirus Activity of 6–Anilino–9–benxyl–2–chloro–9H–purines", J. Med. Chem., 1990, vol. 33, pp. 1360–1363, XP–002140324.

Kozhevnikov, "Synthesis of nitro and amino derivatives of 2–methyl–3–aryl–4–quinazoline", Chemical Abstracts, Abstract No. 19599, vol. 077, no. 3, Jul. 17, 1972, XXP002138275.

Kuboto et al.; Abstract No. 84:45269, Japan 50105558, Aug. 1975.

Lesiak, "New amides of pyrrole–N– and indole–N–caboxylic acids", Chemical Abstracts, No. 126704v, XP–002121335.

Makoto; "Amide and Its Use"; Patent Abstracts of Japan, Abstract No. 09124571, May 13, 1997, *also attached*: Abstract (Derwent); XP 002086154.

Mühlbach, "Pyrazoles—A Novel Class of Blocking Agents for Isocyanates", Journal of Polymer Science: Part A: Polymer Chemistry, vol. 32, Mar. 1994, pp. 753–765.

Myers et al., "The Preparation of SAR of 4–(Anilino), 4–(Phenoxy), and 4–(Thiophenoxy)–Quniazoline: Inhibitors of P56$^{lck}$ and EGF–R Tyrosine Kinase Activity", Bioorganic & Medicinal Chemistry Letters, vol. 7, No. 4, pp. 417–420.

Parmer et al., "Synthesis of substituted quinozoline hydrazides: the relation between chemical structure and monoamine oxidase inhibitory activity", Chemical Abstract No. 59182, vol. 069, No. 15, Oct. 7, 1968, XP002138276.

Petrova et al., "Determination of the Structure of the Oxidative . . . by Spectroscopic Methods", Journal of Molecular Structure, vol. 142, 1986, pp. 459–462.

Sugawara et al., Kogyo Kaguku Zasshi 72(11) 2425–2429, 1969, Chemical Abstract: 72:66514, 1970.

Thompson et al., "Tyrosine Kinase Inhibitors. 7.7–Amino–4–(phenylamino– and 7–Amino–4–[(phenylmethyl)amino]purido 4,3–d pyrimidines: A New Class of Inhibitors of the Tyrosine Kinase Activity of the Epidermal Growth Factor Receptor"; Journal of Medicinal Chemistry, US, American Chemical Society, vol. 39, No. 19, 1995, pp. 3780–3788, XP002140323.

Wang et al., "Low–valent Titanium–induced Reactions of Substituted Nitrobenzenes", J. Chem. Research, 1998, pp. 182–183.

SUBSTITUTED ANILINO-QUINOLINE COMPOUNDS AND USE THEREOF

This is a Divisional of application Ser. No. 09/787,883, filed Mar. 23, 2001; now U.S. Pat. No. 6,593,333 which is a PCT National Phase Application of PCT/GB99/03220 filed Sep. 27, 1999, which claims priority to GB Application No. 982133.2 filed Oct. 1, 1998 and GB Application No. 9906564 filed Mar. 23, 1999. Each listed U.S. Patents and/or application is entirely incorporated herein by reference in its entirety.

This invention concerns certain amide derivatives and their use as inhibitors of cytokine mediated disease. The invention also concerns processes for the manufacture of said novel amide derivatives, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as congestive heart disease, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*. 1997 7, 729–733. p38 kinase is known to exist in isoforms identified as p38α and p38β.

European Patent Application No. 0 566 226, discloses certain quinazoline compounds as tyrosine kinase-inhibiting anticancer agents including the compounds:
4-(3-acetamidoanilino)-6,7-dimethoxyquinazoline and
4-(3-benzamidoanilino)-6,7-dimethoxyquinazoline.

The compounds disclosed in the present invention are inhibitors of the production of cytokines such as TNF, in particular of TNFα, and various interleukins, in particular IL-1.

According to one aspect of the present invention there is provided a compound of the Formula (I):

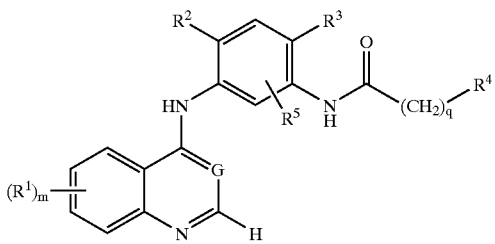

wherein:

G is N or CH;

$R^1$ is hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$- (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, or $R^1$ is of the Formula (IA):

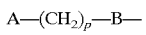

wherein A is halo, hydroxy, $C_{1-6}$alkoxy, $C_{1-6}$alkylS(O)$_n$- (wherein n is 0–2), cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and B is a bond, oxy, imino, N-($C_{1-6}$alkyl)imino or —C(O)NH—, with the proviso that p is 2 or more unless B is a bond or —C(O)NH—, or $R^1$ is of the Formula (IB):

wherein D is aryl, heteroaryl or heterocyclyl and E is a bond, $C_{1-6}$alkylene, $C_{1-6}$alkeneoxy, oxy, imino, N-($C_{1-6}$alkyl)imino, $C_{1-6}$alkyleneimino, N-($C_{1-6}$alkyl)-$C_{1-6}$alkyleneimino, $C_{1-6}$alkyleneoxy-$C_{1-6}$alkylene, $C_{1-6}$alkyleneimino-$C_{1-6}$alkylene, N-($C_{1-6}$alkyl)-$C_{1-6}$alkyleneimino-$C_{1-6}$alkylene, —C(O)NH—, —SO$_2$NH—, —NHSO$_2$— or $C_{2-6}$alkanoylimino, and any aryl, heteroaryl or heterocyclyl group in a $R^1$ group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-($C_{1-6}$alkyl)$_2$carbamoyl, $C_{2-6}$alkanoyl, amino, N-$C_{1-6}$alkylamino and N,N-($C_{1-6}$alkyl)$_2$amino, and any heterocyclyl group in a $R^1$ group may be optionally substituted with one or two oxo or thioxo substituents, and any of the $R^1$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^2$ is hydrogen, halo, $C_{1-6}$alkyl, $C_{2-6}$alkenyl or $C_{2-6}$alkynyl;
$R^3$ is hydrogen, halo, $C_{1-6}$alkyl, $C_{2-6}$alkenyl or $C_{2-6}$alkynyl;

$R^4$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy$C_{2-6}$alkoxy, amino$C_{2-6}$alkoxy, N-$C_{1-6}$alkylamino$C_{2-6}$alkoxy, N,N-($C_{1-6}$alkyl)$_2$amino$C_{2-6}$alkoxy or $C_{3-7}$cycloalkyl, or $R^4$ is of the Formula (IC):

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —SO$_2$NH—, —NHSO$_2$— or —NHC(O)—$C_{1-6}$alkylene-, and any aryl, heteroaryl or heterocyclyl group in a $R^4$ group may be optionally substituted by one or more groups selected from hydroxy, halo, trifluoromethyl, cyano, mercapto, nitro, amino carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^4$ group may be optionally substituted with one or more groups of the Formula (IA'):

wherein $A^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—;

or any aryl, heteroaryl or heterocyclyl group in a $R^4$ group may be optionally substituted with one or more groups of the Formula (IB'):

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a substituent on $R^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-($C_{1-6}$alkyl)$_2$carbamoyl, $C_{2-6}$alkanoyl, amino, N-$C_{1-6}$alkylamino and N,N-($C_{1-6}$alkyl)$_2$amino, and any $C_{3-7}$cycloalkyl or heterocyclyl group in a $R^4$ group may be optionally substituted with one or two oxo or thioxo substituents, and any of the $R^4$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^5$ is hydrogen, halo, trifluoromethyl, cyano, nitro, amino, hydroxy, $C_{1-6}$alkyl, $C_{2-6}$alkenyl, $C_{2-6}$alkynyl, $C_{1-6}$alkoxy, N-$C_{1-6}$alkylamino or N,N-($C_{1-6}$alkyl)$_2$amino;

m is 1, 2 or 3; and q is 0, 1, 2, 3 or 4;

or a pharmaceutically acceptable salt or an in vivo cleavable ester thereof; with the proviso that:
4-(3-acetamidoanilino)-6,7-dimethoxyquinazoline; and
4-(3-benzamidoanilino)-6,7-dimethoxyquinazoline are excluded.

According to a further aspect of the present invention there is provided a compound of the Formula (I) wherein:

G is N or CH;

$R^1$ is hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-4}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, or $R^1$ is of the formula:

A—(CH$_2$)$_p$—B—  (IA)

wherein A is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and B is a bond, oxy, imino, N-($C_{1-6}$alkyl)imino or —C(O)NH—, with the proviso that p is 2 or more unless B is a bond or —C(O)NH—, or $R^1$ is of the formula:

D—E—  (IB)

wherein D is aryl, heteroaryl or heterocyclyl and E is a bond, $C_{1-6}$alkylene, $C_{1-6}$alkyleneoxy, oxy, imino, N-($C_{1-6}$alkyl)imino, $C_{1-6}$alkyleneimino, N-($C_{1-6}$alkyl)-$C_{1-6}$alkyleneimino, —C(O)NH—, —SO$_2$NH—, —NHSO$_2$— or $C_{2-6}$alkanoylimino, and any aryl, heteroaryl or heterocyclyl group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$carbamoyl, $C_{2-6}$alkanoyl, amino, N-$C_{1-6}$alkylamino and N,N-($C_{1-6}$alkyl)$_2$amino;

$R^2$ is hydrogen, halo, $C_{1-6}$alkyl, $C_{2-6}$alkenyl or $C_{2-6}$alkynyl;

$R^3$ is hydrogen, halo, $C_{1-6}$alkyl, $C_{2-6}$alkenyl or $C_{2-6}$alkynyl;

$R^4$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy$C_{2-6}$alkoxy, amino$C_{2-6}$alkoxy, N-$C_{1-6}$alkylamino$C_{2-6}$alkoxy, N,N-($C_{1-6}$alkyl)$_2$amino$C_{2-6}$alkoxy or $C_{3-7}$cycloalkyl, or $R^4$ is of the formula:

—K—J  (IC)

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —SO$_2$NH—, —NHSO$_2$— or —NHC(O)—$C_{1-6}$alkylene-, and any aryl, heteroaryl or heterocyclyl group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl may be optionally substituted with one or more groups of the formula (IA'):

—B$^1$-(CH$_2$)$_p$—A$^1$  (IA')

wherein A$^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and B$^1$ is a bond, oxy, imino, N-($C_{1-6}$alkyl)imino or —NHC(O)—, with the proviso that p is 2 or more unless B$^1$ is a bond or —NHC(O)—;

and/or (IB'):

—E$^1$—D$^1$  (IB')

wherein D$^1$ is aryl, heteroaryl or heterocyclyl and E$^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-($C_{1-6}$alkyl)$_2$carbamoyl, $C_{2-6}$alkanoyl, amino, N-$C_{1-6}$alkylamino and N,N-($C_{1-6}$alkyl)$_2$amino;

$R^5$ is hydrogen, halo, trifluoromethyl, cyano, nitro, amino, hydroxy, $C_{1-6}$alkyl, $C_{2-6}$alkenyl, $C_{2-6}$alkynyl, $C_{1-6}$alkoxy, N-$C_{1-6}$alkylamino or N,N-($C_{1-6}$alkyl)$_2$amino;

m is 1, 2 or 3;

q is 0, 1, 2, 3 or 4;

or a pharmaceutically acceptable salt or an in vivo cleavable ester thereof; with the proviso that:
4-(3-acetamidoanilino)-6,7-dimethoxyquinazoline; and
4-(3-benzamidoanilino)-6,7-dimethoxyquinazoline are excluded.

In this specification the term "alkyl" includes both straight and branched chain alkyl groups but references to individual alkyl groups such as "propyl" are specific for the straight chain version only. For example, "$C_{1-6}$alkyl" includes propyl, isopropyl and tert-butyl. However, references to individual alkyl groups such as 'propyl' are specific for the straight chained version only and references to individual branched chain alkyl groups such as 'isopropyl' are specific for the branched chain version only. A similar convention applies to other radicals, for example "amino$C_{2-6}$alkoxy" includes 2-aminoethoxy, 2-aminopropoxy and 3-amino-2-methylpropoxy. The term "halo" refers to fluoro, chloro, bromo and iodo.

The term "aryl" refers to phenyl or naphthyl.

The term "heteroaryl" refers to, unless otherwise further specified, a monocyclic-, bicyclic- or tricyclic-5–14 membered ring that contains some degree of unsaturation, with up to five ring heteroatoms selected from nitrogen, oxygen and sulphur wherein a —CH$_2$— group can optionally be replaced by a —C(O)—, a ring nitrogen atom may optionally bear a $C_{1-6}$alkyl group or a ring nitrogen atom may be optionally oxidised to form the N-oxide. Examples of "heteroaryt" include thienyl, furyl, pyranyl, pyrrolyl, imidazolyl, pyrazolyl, thiazolyl, oxazolyl, isoxazolyl, pyridyl, pyridyl-N-oxide, oxopyridyl, oxoquinolyl, pyrimidinyl, pyrazinyl, oxopyrazinyl, pyridazinyl, indolyl, benzofuranyl, benzimidazolyl, benzothiazolyl, quinolyl, N-methyloxoquinolyl, isoquinolinyl, quinazolinyl, xanthenyl, quinoxalinyl, indazolyl, benzofuranyl and cinnolinolyl.

The term "heterocyclyl" refers to, unless otherwise further specified, a mono- or bicyclic-5–14 membered ring, that is totally saturated, with up to five ring heteroatoms selected from nitrogen, oxygen and sulphur wherein a —CH$_2$— group can optionally be replaced by a —C(O)— or a ring nitrogen atom may optionally bear a C$_{1-6}$alkyl group. Examples of such heterocyclyls include morpholinyl, N-methylmorpholinyl, pyrrolidinyl, imidazolidinyl, pyrazolidinyl, piperidinyl, homopiperidinyl, N-methylpiperidinyl, piperazinyl, homopiperazinyl and quinuclidinyl.

Where optional substituents are chosen from "one or more" groups it is to be understood that this definition includes all substituents being chosen from one of the specified groups or the substituents being chosen from two or more of the specified groups. Conveniently there may be possible combinations of substituents include 1) a bromo group, 2) two chloro groups, 3) a methoxy, ethoxy and propoxy substituent, 4) a fluoro and a methoxy group, 5) a methoxy, a methyl and an ethyl group, and 6) a chloro, a methoxy and an ethyl group.

It is to be understood that the bicyclic ring within the compound of Formula (I) is shown with a hydrogen atom attached to the carbon between the N atom and G group in order to indicate that this position is unsubstituted. Thereby it is to be understood that that hydrogen atom may not be replaced by a R$^1$ substituent. It should also be understood however that when G is a CH group such that the bicyclic ring is a quinoline ring the 3-position of the quinoline ring may bear any one of the R$^1$ substituents.

The following table gives examples of radicals that fall within the definition of the generic terms used in this specification:

| Generic Term | Example of Radical |
|---|---|
| C$_{1-4}$alkyl | methyl, ethyl, isopropyl |
| C$_{1-6}$alkoxycarbonyl | methoxycarbonyl, ethoxycarbonyl, n- and tert-butoxycarbonyl |
| C$_{1-6}$alkoxy | methoxy, ethoxy, propoxy |
| C$_{1-4}$alkoxy | methoxy, ethoxy, propoxy |
| C$_{2-4}$alkoxy | ethoxy, propoxy, t-butoxy |
| C$_{1-6}$alkanoylamino | formamido, acetamido, propionylamino |
| C$_{1-6}$alkylS(O)$_n$ where n is 0–2 | methylthio, ethylthio, methylsulphinyl, ethylsulphinyl, mesyl, ethylsulphonyl |
| C$_{2-6}$alkanoyl | propionyl, acetyl |
| N-C$_{1-6}$alkylamino | N-methylamino, N-ethylamino |
| N,N-(C$_{1-6}$alkyl)$_2$amino | N,N-dimethylamino, N,N-diethylamino, N-ethyl-N-methylamino |
| C$_{1-6}$alkoxyC$_{2-6}$alkoxy | 2-methoxyethoxy, 4-propoxybutoxy |
| N-(C$_{1-6}$alkyl)aminoC$_{2-6}$alkoxy | 3-(N-methylamino)propoxy, 4-(N-ethylamino)butoxy |
| N,N-(C$_{1-6}$alkyl)$_2$aminoC$_{2-6}$alkoxy | 2-(N,N-dimethylamino)ethoxy, 3-(N-methyl-N-ethylamino)propoxy |
| C$_{3-7}$cycloalkyl | cyclopropyl, cyclohexyl |
| C$_{2-6}$alkenyl | vinyl, allyl, 1-propenyl |
| C$_{2-6}$alkynyl | ethynyl, 1-propynyl, 2-propynyl |
| hydroxyC$_{2-6}$alkoxy | 2-hydroxyethoxy, 2-hydroxypropoxy |
| C$_{1-6}$alkylsulphonylamino | methanesulphonamido, ethanesulphonamido |
| C$_{1-6}$alkylsulphonyl-N-(C$_{1-6}$alkyl)amino | N-ethylmethanesulphonamido, N-butylethanesulphonamido |
| N-(C$_{1-6}$alkyl)sulphamoyl | N-methylsulphamoyl, N-ethylsulphamoyl |
| N,N-(C$_{1-6}$alkyl)$_2$sulphamoyl | N,N-dimethylsulphamoyl, N-methyl-N-ethylsulphamoyl |
| N-(C$_{1-6}$alkyl)carbamoyl | N-methylcarbamoyl, N-ethylcarbamoyl |
| N,N-(C$_{1-6}$alkyl)$_2$carbamoyl | N,N-dimethylcarbamoyl, N-methyl-N-ethylcarbamoyl |
| C$_{1-6}$alkanoyloxy | propionyloxy, acetyloxy, formyloxy |
| —O—C$_{1-3}$alkyl-O— | methylenedioxy, ethylenedioxy (i.e. a bidentate substituent, attached to the ring in two adjacent positions) |

1, 2 or 3 such optional substituents. For example, where optional substituents are chosen from one or more groups selected from halo, C$_{1-6}$alkoxy and C$_{1-6}$alkyl, examples of In the linking groups B, E, B$^1$, E$^1$ and K that fall within the definition of R$^1$ and R$^4$, the following table gives examples of radicals that fall within these general terms:

| Generic Term | Example of Radical |
|---|---|
| C$_{1-6}$alkylene | —CH$_2$CH$_2$—, —CH$_2$CH(CH$_3$)CH$_2$— |
| C$_{1-6}$alkyleneoxy | —CH$_2$CH$_2$O—, —CH$_2$CH(CH$_3$)CH$_2$O— |
| N-(C$_{1-6}$alkyl)imino | —N(Me)—, —N($^i$Pr)— |
| C$_{1-6}$alkyleneimino | —CH$_2$CH$_2$NH—, —CH$_2$CH(CH$_3$)CH$_2$NH— |
| N-(C$_{1-6}$alkyl)-C$_{1-6}$alkyleneimino | —CH$_2$CH$_2$N(Me)—, —CH$_2$CH(CH$_3$)CH$_2$N($^i$Pr)— |

| Generic Term | Example of Radical |
|---|---|
| $C_{2-6}$alkanoylimino | —$CH_2CH_2C(O)NH$—, —$CH_2CH(CH_3)CH_2C(O)NH$— |
| oxy$C_{1-6}$alkylene | —$OCH_2CH_2$—, —$OCH_2CH(CH_3)CH_2$— |
| imino$C_{1-6}$alkylene | —$NHCH_2CH_2$—, —$NHCH_2CH(CH_3)CH_2$— |
| N-($C_{1-6}$alkyl)imino$C_{1-6}$alkylene | —$N(Me)CH_2CH_2$—, —$N(^iPr)CH_2CH(CH_3)CH_2$— |
| —$NHC(O)C_{1-6}$alkylene- | —$NHC(O)CH_2CH_2$—, —$NHC(O)CH_2CH(CH_3)CH_2$— |

For the avoidance of doubt, it is to be understood that when, for example, $R^1$ is a group of the Formula (IB):

D—E—          (IB)

and the linking group E is, for example, a $C_{1-6}$alkyleneoxy group such as —$CH_2CH_2O$—, it is a $CH_2$ group which is attached to D and the O atom which is attached to the bicyclic ring within Formula (I). Similarly when, for example, $R^4$ is a group of the Formula (IB'):

—$E^1$—$D^1$          (IB')

and the linking group $E^1$ is, for example, an imino$C_{1-6}$alkylene group such as —$NHCH_2CH_2$—, it is a $CH_2$ group which is attached to $D^1$ and the NH group which is attached to the bicyclic ring within Formula (I). An analogous convention applies to other bidentate linking groups.

It is to be understood that, insofar as certain of the compounds of the Formula (I) defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Preferable values of $R^1$, $R^2$, $R^3$, $R^4$, $R^5$, G, q and m are as follows.

Preferably $R^1$ is hydroxy, halo, $C_{1-6}$alkoxy, N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, heterocyclyl$C_{1-6}$alkyl, heterocyclyl$C_{1-6}$alkoxy, heterocyclyloxy, heterocyclyl$C_{1-6}$alkylamino$C_{1-6}$alkyl or heteroaryl$C_{1-6}$alkoxy.

More preferably $R^1$ is hydroxy, halo, $C_{1-6}$alkoxy, N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{6}$alkylamino, N,N-($C_{1-6}$alkyl)$_2$amino$C_{1-6}$alkylamino$C_{1-6}$alkyl, piperazin-1-yl$C_{1-6}$alkyl, 4-$C_{1-6}$alkylpiperazin-1-yl$C_{1-6}$alkyl, homopiperazinyl-1-yl$C_{1-6}$alkyl, 4-$C_{1-6}$alkylhomopiperazinyl-1-yl$C_{1-6}$alkyl, pyrrolidinyl$C_{1-6}$alkoxy, piperidinyl$C_{1-6}$alkoxy, N-($C_{1-6}$alkyl) pyrrolidinyl$C_{1-6}$alkoxy, N-($C_{1-6}$alkyl)piperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$alkoxy, homopiperazinyl$C_{1-6}$alkoxy, N-($C_{1-6}$alkyl)homopiperazinyl $C_{1-6}$alkoxy, pyrrolidinyloxy, piperidinyloxy, morpholinyl$C_{1-6}$alkylamino$C_{1-6}$alkyl or pyridyl$C_{1-6}$alkoxy.

More particularly $R^1$ is methoxy, 2-dimethylaminoethoxy, 2-diethylaminoethoxy, 2-diisopropylaminoethoxy, 3-dimethylaminopropoxy, 3-diethylaminopropoxy, 2-morpholinoethoxy, 3-morpholinopropoxy, 2-piperidinoethoxy, N-methylpiperidin-2-ylmethoxy, N-methylpiperidin-3-ylmethoxy, 2-pyrrolidin-1-ylethoxy, 2-(N-methylpyrrolidin-2-yl)ethoxy, N-methyl-5-oxopyrrolidin-2-ylmethoxy, 3-pyrrolidin-1-ylpropoxy, 2-(2-oxoimidazolidin-1-yl)ethoxy, 2-(4-methylpiperazin-1-yl) ethoxy or 3-pyrid-3-ylpropoxy.

Further more particularly $R^1$ is methoxy, 2-diisopropylaminoethoxy, 3-diethylaminopropoxy, 3-morpholinopropoxy or 3-pyrrolidin-1-ylpropoxy.

More preferably $R^1$ is $C_{1-6}$alkoxy, heterocyclyl$C_{1-6}$alkoxy or heteroaryl$C_{1-6}$alkoxy.

More preferably $R^1$ is $C_{1-6}$alkoxy, morpholinyl$C_{1-6}$alkoxy, pyrrolidinyl$C_{1-6}$alkoxy, pyridyl$C_{1-6}$alkoxy, piperidin-1-yl$C_{1-6}$alkoxy, piperazin-1-yl$C_{1-6}$alkoxy or 4-$C_{1-6}$alkylpiperazinyl-1-yl$C_{1-6}$alkoxy.

Particularly $R^1$ is $C_{1-4}$alkoxy, morpholinyl$C_{2-4}$alkoxy, pyrrolidinyl$C_{2-4}$alkoxy or pyridyl$C_{2-4}$alkoxy.

More particularly $R^1$ is methoxy, 2-morpholinoethoxy, 3-morpholinopropoxy, 2-pyrrolidin-1-ylethoxy or 3-pyrid-3-ylpropoxy.

Preferably $R^2$ is hydrogen, $C_{1-6}$alkyl or halo.
More preferably $R^2$ is hydrogen, $C_{1-4}$alkyl or halo.
Particularly $R^2$ is hydrogen, methyl, fluoro or chloro.
More particularly $R^2$ is $C_{1-4}$alkyl or halo when $R^3$ is hydrogen.

Preferably $R^3$ is hydrogen, $C_{1-6}$alkyl or halo.
More preferably $R^3$ is hydrogen, $C_{1-4}$alkyl or halo.
Particularly $R^3$ is hydrogen, methyl, fluoro or chloro.
More particularly $R^3$ is $C_{1-4}$alkyl or halo when $R^2$ is hydrogen.

Preferably $R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino or heterocyclyl.

More preferably $R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino, pyrrolidin-1-yl, piperidinyl, morpholino, piperazinyl, 4-$C_{1-6}$alkylpiperazin-1-yl, homopiperazinyl-1-yl or 4-$C_{1-6}$alkylhomopiperazinyl-1-yl.

More preferably $R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino, piperazinyl, morpholino or piperazinyl.

More preferably $R^4$ is hydrogen or $C_{1-4}$alkoxy or $R^4$ is phenyl, thienyl, furyl, oxazolyl, isoxazolyl, pyrimidyl or pyridyl optionally substituted by one or two halo, cyano, $C_{1-4}$alkyl, $C_{1-4}$alkoxy, N,N-($C_{1-4}$alkyl)$_2$amino, piperidinyl, morpholino or piperazinyl.

Particularly $R^4$ is hydrogen or methoxy or $R^4$ is phenyl, furyl, isoxazolyl or pyridyl optionally substituted by one or more groups selected from fluoro, chloro, cyano, methyl, methoxy, N,N-dimethylamino or morpholino.

More particularly $R^4$ is hydrogen, methoxy, phenyl, 2-methylphenyl, 3-(N,N-dimethylamino)phenyl, 3-fluorophenyl, 3-methoxyphenyl, 4-cyanophenyl, 3,4-dimethoxyphenyl, 3-morpholinophenyl, 2-furyl, 2-chloropyrid-5-yl, 2-morpholinopyrid-4-yl or isoxazol-5-yl.

Further more particularly $R^4$ is pyridyl optionally substituted by a N,N-dimethylamino, N,N-diethylamino, pyrrolidin-1-yl, piperidino or morpholino group.

Even more particularly $R^4$ is 2-morpholinopyrid-4-yl.

Preferably $R^5$ is hydrogen.

Preferably G is N.

Preferably m is 2 or 3.

Particularly m is 1, 2 or 3.

Preferably q is 0 or 1.

When, as defined hereinbefore, any of the $R^1$ or $R^4$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl, suitable substituents so formed include, for example, substituted heterocyclyl$C_{1-6}$alkoxy groups such as 2-hydroxy-3-piperidinopropoxy and 2-hydroxy-3-morpholinopropoxy, substituted amino$C_{1-6}$alkoxy groups such as 3-amino-2-hydroxypropoxy, substituted N-$C_{1-6}$alkylamino$C_{1-6}$alkoxy groups such as 2-hydroxy-3-methylaminopropoxy, substituted N,N-($C_{1-6}$alkyl)$_2$amino$C_{1-6}$alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl$C_{1-6}$alkylamino groups such as 2-hydroxy-3-piperidinopropylamino and 2-hydroxy-3-morpholinopropylamino, substituted amino$C_{1-6}$alkylamino groups such as 3-amino-2-hydroxypropylamino, substituted N-$C_{1-6}$alkylamino$C_{1-6}$alkylamino groups such as 2-hydroxy-3-methylaminopropylamino, substituted N,N-($C_{1-6}$alkyl)$_2$amino$C_{1-6}$alkylamino groups such as 3-dimethylamino-2-hydroxypropylamino, 3-[N-(3-dimethylaminopropyl)-N-methylamino]propylamino and 3-[N-(3-dimethylaminopropyl)-N-methylamino]-2-hydroxypropylamino, substituted N-$C_{1-6}$alkylamino$C_{1-6}$alkyl groups such as 2-dimethylaminoethylaminomethyl, 3-dimethylaminopropylaminomethyl, 3-dimethylamino-2,2-dimethylpropylaminomethyl, 2-morpholinoethylaminomethyl, 2-piperazin-1-ylethylaminomethyl and 3-morpholinopropylaminomethyl.

Preferred combinations of q and $R^4$ are as follows.

When q is 0, preferably $R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino, piperazinyl, morpholino or piperazinyl. When q is 1, preferably $R^4$ is hydrogen or $C_{1-6}$alkoxy. When q is 2 preferably $R^4$ is hydrogen.

When q is 0, more preferably $R^4$ is hydrogen or $C_{1-4}$alkoxy or $R^4$ is phenyl, thienyl, furyl, oxazolyl, isoxazolyl, pyrimidyl or pyridyl optionally substituted by one or two halo, cyano, $C_{1-4}$alkyl, $C_{1-4}$alkoxy, N,N-($C_{1-4}$alkyl)$_2$amino, piperazinyl, morpholino or piperazinyl groups. When q is 1, more preferably $R^4$ is hydrogen or $C_{1-4}$alkoxy.

When q is 0, particularly $R^4$ is hydrogen or methoxy or $R^4$ is phenyl, furyl, isoxazolyl or pyridyl optionally substituted by one or more groups selected from fluoro, chloro, cyano, methyl, methoxy, N,N-dimethylamino or morpholino. When q is 1, particularly $R^4$ is hydrogen or methoxy.

When q is 0, more particularly $R^4$ is hydrogen, methoxy, phenyl, 2-methylphenyl, 3-(N,N-dimethylamino)phenyl, 3-fluorophenyl, 3-methoxyphenyl, 4-cyanophenyl, 3,4-dimethoxyphenyl, 3-morpholinophenyl, 2-furyl, 2-chloropyrid-5-yl, 2-morpholinopyridyl-4-yl or isoxazol-5-yl.

Preferred combinations of $R^1$ and m are as follows.

When m is 2, preferably $R^1$ is $C_{1-6}$alkoxy, heterocyclyl$C_{1-6}$alkoxy or heteroaryl$C_{1-6}$alkoxy. When m is 3, preferably $R^1$ is $C_{1-6}$alkoxy.

When m is 2, more preferably $R^1$ is $C_{1-4}$alkoxy, morpholinyl$C_{2-4}$alkoxy, pyrrolidinyl$C_{2-4}$alkoxy or pyridyl$C_{2-4}$alkoxy. When m is 3, preferably $R^1$ is $C_{1-4}$alkoxy.

When m is 2 particularly $R^1$ is methoxy, 2-morpholinoethoxy, 3-morpholinopropoxy, 2-pyrrolidin-1-ylethoxy or 3-pyrid-3-ylpropoxy. When m is 3, particularly $R^1$ is methoxy.

When m is 2 more particularly $(R^1)_m$ is 6,7-dimethoxy, 6-methoxy-7-[2-morpholinoethoxy], 6-methoxy-7-[3-morpholinopropoxy], 6-methoxy-7-(2-pyrrolidin-1-ylethoxy) or 6-methoxy-7-(3-pyrid-3-ylpropoxy). When m is 3, more particularly $(R^1)_m$ is 6, 7, 8-trimethoxy.

In one embodiment of the invention $R^4$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy-$C_{2-6}$alkoxy, amino$C_{2-6}$alkoxy, N-$C_{1-6}$alkylamino$C_{2-6}$alkoxy or N,N-($C_{1-6}$alkyl)$_2$amino-$C_{2-6}$alkoxy.

In a further embodiment of the invention $R^4$ is of the Formula:

$$—K—J \qquad (IC)$$

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —SO$_2$NH—, —NHSO$_2$— or —NHC(O)—$C_{1-6}$alkylene-, and any aryl, heteroaryl or heterocyclyl may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl may be optionally substituted with one or more groups of the Formula (IA') or (IB') wherein $A^1$, $B^1$, $D^1$ and $E^1$ are as defined for Formula (I).

In another embodiment of the invention G is CH.

Another aspect of the present invention provides a compound of the Formula (I) (as depicted above) wherein:

$R^1$ is hydroxy, halo, $C_{1-6}$alkoxy, N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, heterocyclyl$C_{1-6}$alkyl, heterocyclyl-$C_{1-6}$alkoxy, heterocyclyloxy, heterocyclyl$C_{1-6}$alkylamino$C_{1-6}$alkyl or heteroaryl$C_{1-6}$alkoxy;

$R^2$ is hydrogen, $C_{1-6}$alkyl or halo;

$R^3$ is hydrogen, $C_{1-6}$alkyl or halo;

$R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino or heterocyclyl;

$R^5$ is hydrogen;

G is N;

m is 1, 2 or 3; and q is 0 or 1;

or a pharmaceutically acceptable salt, or an in vivo cleavable ester thereof.

A further aspect of the present invention provides a compound of the Formula (I) (as depicted above) wherein:

$R^1$ is hydroxy, halo, $C_{1-6}$alkoxy, N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, piperazin-1-yl$C_{1-6}$alkyl, 4-$C_{1-6}$alkylpiperazin-1-yl$C_{1-6}$alkyl, homopiperazinyl-1-yl$C_{1-6}$alkyl, 4-$C_{1-6}$alkylhomopiperazinyl-1-yl$C_{1-4}$alkyl, pyrrolidinyl$C_{1-6}$alkoxy, piperidinyl$C_{1-6}$alkoxy, N-($C_{1-6}$alkyl)pyrrolidinyl$C_{1-6}$alkoxy, N-($C_{1-6}$alkyl)piperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$alkoxy, homopiperazinyl$C_{1-6}$alkoxy, N-($C_{1-6}$alkyl)homopiperazinyl$C_{1-6}$alkoxy, pyrrolidinyloxy, piperidinyloxy, morpholinyl$C_{1-6}$alkylamino$C_{1-6}$alkyl or pyridyl$C_{1-6}$alkoxy;

$R^2$ is hydrogen, $C_{1-6}$alkyl or halo;

$R^3$ is hydrogen, $C_{1-6}$alkyl or halo;

$R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino, pyrrolidin-1-yl, piperidinyl, morpholino, piperazinyl, 4-$C_{1-6}$alkylpiperazin-1-yl, homopiperazinyl-1-yl or 4-$C_{1-6}$alkylhomopiperazinyl-1-yl;

$R^5$ is hydrogen;

G is N;

m is 1, 2 or 3; and q is 0 or 1;

or a pharmaceutically acceptable salt, or an in vivo cleavable ester thereof.

A further aspect of the present invention provides a compound of the Formula (I) (as depicted above) wherein:

$R^1$ is $C_{1-6}$alkoxy, heterocyclyl$C_{1-6}$alkoxy or heteroaryl$C_{1-6}$alkoxy;

$R^2$ is hydrogen, $C_{1-6}$alkyl or halo;

$R^3$ is hydrogen, $C_{1-6}$alkyl or halo;

$R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy or N,N-($C_{1-6}$alkyl)$_2$amino;

$R^5$ is hydrogen;

G is N;

m is 2 or 3; and q is 0 or 1;

or a pharmaceutically acceptable salt, or an in vivo cleavable ester thereof.

A further aspect of the present invention provides a compound of the Formula (I) (as depicted above) wherein:

$R^1$ is $C_{1-6}$alkoxy, morpholinyl$C_{1-6}$alkoxy, pyrrolidinyl$C_{1-6}$alkoxy or pyridyl$C_{1-6}$alkoxy;

$R^2$ is hydrogen, $C_{1-6}$alkyl or halo;

$R^3$ is hydrogen, $C_{1-6}$alkyl or halo;

$R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino, piperidinyl, morpholino or piperazinyl;

$R^5$ is hydrogen;

G is N;

m is 2 or 3; and q is 0 or 1;

or a pharmaceutically acceptable salt, or an in vivo cleavable ester thereof.

An additional aspect of the present invention provides a compound of the Formula (I) (as depicted above) wherein:

$R^1$ is $C_{1-4}$alkoxy, morpholinyl$C_{2-4}$alkoxy, pyrrolidinyl$C_{2-4}$alkoxy or pyridyl$C_{2-4}$alkoxy;

$R^2$ is hydrogen, methyl, fluoro or chloro;

$R^3$ is hydrogen, methyl, fluoro or chloro;

$R^4$ is hydrogen or methoxy or $R^4$ is phenyl, furyl, isoxazolyl or pyridyl optionally substituted by one or more groups selected from fluoro, chloro, cyano, methyl, methoxy, N,N-dimethylamino or morpholino;

$R^5$ is hydrogen;

G is N;

m is 2 or 3; and q is 0 or 1;

or a pharmaceutically acceptable salt, or an in vivo cleavable ester thereof

A further additional aspect of the present invention provides a compound of the Formula (I) (as depicted above) wherein:

$R^1$ is methoxy, 2-morpholinoethoxy, 3-morpholinopropoxy, 2-pyrrolidin-1-ylethoxy or 3-pyrid-3-ylpropoxy;

$R^2$ is hydrogen, methyl, fluoro or chloro;

$R^3$ is hydrogen, methyl, fluoro or chloro;

$R^4$ is hydrogen, methoxy, phenyl, 2-methylphenyl, 3-(N,N-dimethylamino)phenyl, 3-fluorophenyl, 3-methoxyphenyl, 4-cyanophenyl, 3,4-dimethoxyphenyl, 3-morpholinophenyl, 2-furyl, 2-chloropyrid-5-yl, 2-morpholinopyrid-4-yl or isoxazol-5-yl;

$R^5$ is hydrogen;

G is N;

m is 2 or 3; and q is 0 or 1;

or a pharmaceutically acceptable salt, or an in vivo cleavable ester thereof.

A further additional aspect of the present invention provides a compound of the Formula (I) (as depicted above) wherein:

$R^1$ is methoxy, 2-dimethylaminoethoxy, 2-diethylaminoethoxy, 2-diisopropylaminoethoxy, 3-dimethylaminopropoxy, 3-diethylaminopropoxy, 2-morpholinoethoxy, 3-morpholinopropoxy, 2-piperidinoethoxy, N-methylpiperidin-2-ylmethoxy, N-methylpiperidin-3-ylmethoxy, 2-pyrrolidin-1-ylethoxy, 2-(N-methylpyrrolidin-2-yl)ethoxy, N-methyl-5-oxopyrrolidin-2-ylmethoxy, 3-pyrrolidin-1-ylpropoxy, 2-(2-oxoimidazolidin-1-yl)ethoxy, 2-(4-methylpiperazin-1-yl)ethoxy or 3-pyrid-3-ylpropoxy;

$R^2$ is hydrogen, methyl, fluoro or chloro;

$R^3$ is hydrogen, methyl, fluoro or chloro;

$R^4$ is pyridyl optionally substituted by a N,N-dimethylamino, N,N-diethylamino, pyrrolidin-1-yl, piperidino or morpholino group.

R⁵ is hydrogen;
G is N;
m is 1, 2 or 3; and
q is 0;
or a pharmaceutically acceptable salt, or an in vivo cleavable ester thereof.

Preferred compounds are those of Examples 1–86 or a pharmaceutically acceptable salt or an in vivo cleavable ester thereof.

Especially preferred compounds are those of Examples 18, 20, 23, 26, 31, 33, 34, 36, 40, 44, 45 or 48 or a pharmaceutically acceptable salt or an in vivo cleavable ester thereof.

More especially preferred compounds are those of Examples 56, 58, 60, 61, 62, 63, 64, 65, 66, 68, 69 or 73 or a pharmaceutically acceptable salt or an in vivo cleavable ester thereof.

A further especially preferred compound of the invention is, for example:—
4-(3-benzamido-4-fluoroanilino)-6,7-dimethoxyquinazoline,
6-(2-diisopropylaminoethoxy)-7-methoxy-4-[2-methyl-5-(2-morpholinopyridine-4-carboxamido)anilino]quinazoline,
6-(2-dimethylaminoethoxy)-7-methoxy-4-[2-methyl-5-(2-morpholinopyridine-4-carboxamido)anilino]quinazoline or
6-(3-pyrrolidin-1-ylpropoxy)-7-methoxy-4-[2-methyl-5-(2-morpholinopyridine-4-carboxamido)anilino]quinazoline;
or a pharmaceutically acceptable salt or an in vivo cleavable ester thereof.

A further especially preferred compound of the invention is, for example:—
4-(3-benzamido-4-fluoroanilino)-6,7-dimethoxyquinoline;
or a pharmaceutically acceptable salt or an in vivo cleavable ester thereof.

A suitable pharmaceutically acceptable salt of a compound of the Formula (I) is, for example, an acid-addition salt of a compound of the Formula (I) which is sufficiently basic, for example an acid-addition salt with an inorganic or organic acid such as hydrochloric, hydrobromic, sulphuric, trifluoroacetic, citric or maleic acid; or, for example a salt of a compound of the Formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem. Pharm. Bull., 32, 692 (1984).

Examples of such pro-drugs may be used to form in vivo cleavable esters of a compound of the Formula (I). An in vivo cleavable ester of a compound of the Formula (I) containing a carboxy group is, for example, a pharmaceutically-acceptable ester which is cleaved in the human or animal body to produce the parent acid. Suitable pharmaceutically-acceptable esters for carboxy include $C_{1-6}$alkoxymethyl esters, for example methoxymethyl; $C_{1-6}$alkanoyloxymethylesters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

In order to use a compound of the Formula (I), or a pharmaceutically acceptable salt or in vivo cleavable ester thereof, for the therapeutic treatment (including prophylactic treatment) of mammals including humans, it is normally formulated in accordance with standard pharmaceutical practice as a pharmaceutical composition.

According to this aspect of the invention there is provided a pharmaceutical composition which comprises an amide derivative of the Formula (I), or a pharmaceutically acceptable salt or in vivo cleavable ester thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia: dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parentally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight, preferably 0.5 mg to 40 mg per kg body weight, is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

The compounds of this invention may be used in combination with other drugs and therapies used in the treatment of disease states which would benefit from the inhibition of cytokines, in particular TNF and IL-1. For example, the compounds of the Formula (I) could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula (I) are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicylic acid, ibuprofen, sulindac, tolmetin and piroxicam. Co-administration of a compound of the Formula (I) with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula (I), or a pharmaceutically acceptable salt or in vivo cleavable ester thereof, in conjunction or admixture with a cyclooxygenase inhibitory non-steroidal anti-inflammatory agent, and a pharmaceutically acceptable diluent or carrier.

The compounds of the invention may also be used with anti-inflammatory agents such as an inhibitor of the enzyme 5-lipoxygenase (such as those disclosed in European Patent Applications Nos. 0351194, 0375368, 0375404, 0375452, 0375457, 0381375, 0385662, 0385663, 0385679, 0385680).

The compounds of the Formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula (I) may be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula (I) are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

According to a further aspect of the present invention, there is provided a process for preparing a compound of the Formula (I), or a pharmaceutically acceptable salt or an in vivo cleavable ester thereof, which process (wherein $R^1$, $R^2$, $R^3$, $R^4$, $R^5$, G, m and q are as defined for Formula (I) unless otherwise stated) comprises of:

a) reacting an aniline of the Formula (II):

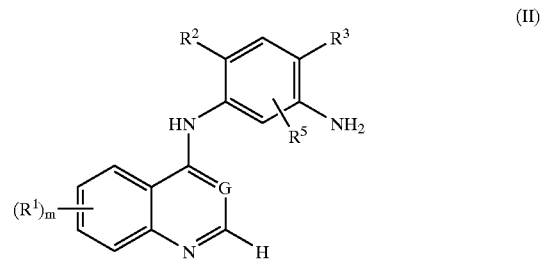

with an acyl compound of the Formula (III):

wherein L is a displaceable group as defined below;

b) reacting an activated heteroaryl of the Formula (IV):

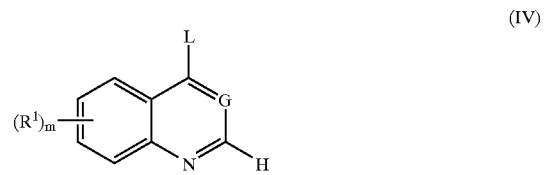

wherein L is a displaceable group as defined below, with an aniline of the Formula (V):

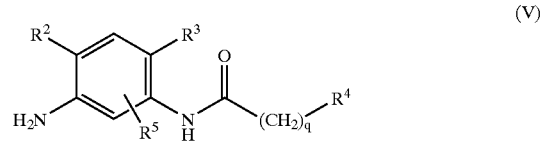

or c) for the preparation of a compound of the Formula (I) wherein $R^1$ or a substituent on $R^4$ is $C_{1-6}$alkoxy or substituted $C_{1-6}$alkoxy, $C_{1-6}$alkylS-, N-$C_{1-6}$alkylamino, N,N-($C_{1-6}$alkyl)$_2$amino or substituted $C_{1-6}$alkylamino, the alkylation, conveniently in the presence of a suitable base as defined below, of an amide derivative of the Formula (I) wherein $R^1$ or a substituent on $R^4$ is hydroxy, mercapto or amino as appropriate; and thereafter if necessary:

i) converting a compound of the Formula (I) into another compound of the Formula (I);
  ii) removing any protecting groups; and
  iii) forming a pharmaceutically acceptable salt or in vivo cleavable ester.

Specific reaction conditions for the above process variants are as follows:—

For process variant a) A suitable displaceable group L is, for example, a halogeno, activated phenoxy group or sulphonyloxy group, for example a chloro, bromo, pentafluorophenoxy or methanesulphonyloxy or toluene-4-sulphonyloxy group. Especially preferred displaceable groups are chloro and pentafluorophenoxy.

Anilines of the Formula (II) and acyl compounds of the Formula (III) may be reacted together in a suitable inert solvent or diluent, for example dichloromethane, acetonitrile, butanol, tetramethylene sulphone, tetrahydrofuran 1,2-dimethoxyethane, N,N-dimethylformamide, N,N-dimethylacetamide or N-methylpyrrolidin-2-one, optionally in the presence of a suitable base, and at a temperature in the range, for example, 0° to 50° C., conveniently at or near room temperature.

A suitable base is, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

Anilines of the Formula (II) may be prepared by the reaction of the activated heteroaryl of the Formula (IV) according to the following scheme:

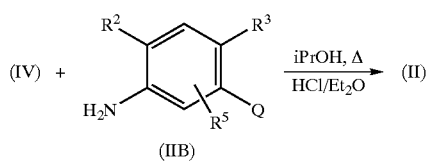

wherein Q is —NH$_2$ or, if R$^2$ and R$^3$ are not identical and a regiospecific reaction is desired, Q can be amino protected by a suitable protecting group (such as those defined below) or nitro, whereafter the protecting group is removed, or the nitro group is reduced (for example with iron powder and acetic acid) to generate the aniline of the Formula (II).

Activated heteroaryls of the Formula (IV) are known compounds, are commercially available or are prepared by processes known in the art. For example where L is chloro as in Formula (IVB) or pentafluorophenoxy as in Formula (IVC), suitable compounds of the Formula (IV) may be prepared by the following scheme from compounds of the Formula (IVA) which are known compounds, are commercially available or are prepared by processes known in the art.:

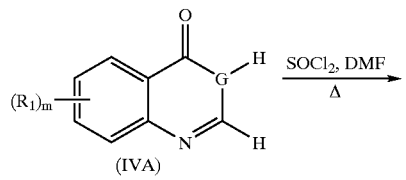

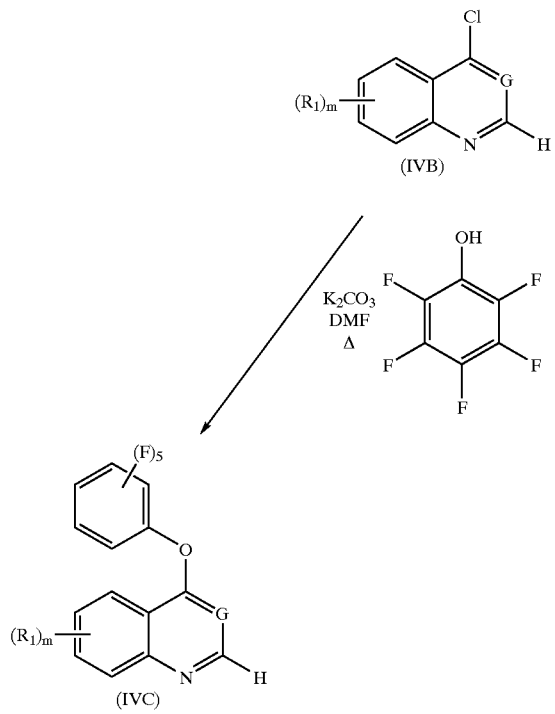

For process variant b) A suitable displaceable group L is as defined above.

Activated heteroaryls of the formula (IV) and anilines of the Formula (V) may be reacted together in the presence of a protic solvent, for example, isopropanol, in the presence of an acid, for example hydrogen chloride gas in diethyl ether, or hydrochloric acid, and at a temperature in the range, for example, 0° to 150° C., conveniently at or near reflux.

Anilines of the Formula (V) are, known compounds, are commercially available, or are made by processes known in the art. For example, anilines of the Formula (V) may be prepared according to the following scheme:

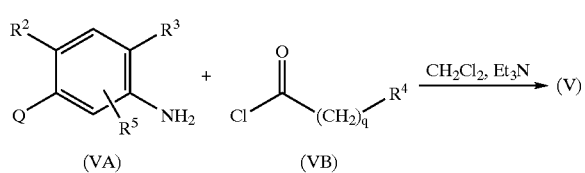

wherein Q is as defined above.

Compounds of the Formulae (IIB), (III), (VA) and (VB) are known compounds, are commercially available or are prepared by processes known in the art.

For process variant c) A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a C$_{1-6}$alkyl chloride, bromide or iodide or a substituted C$_{1-6}$alkyl chloride, bromide or iodide, in the presence of a suitable base and in a suitable inert solvent or diluent as defined above for process variant a).

The reaction is conveniently carried out at a temperature in the range, for example, 10 to 150° C., preferably in the range 20 to 80° C.

Any necessary protecting groups may in general be chosen from any of the groups described in the literature or known to the skilled chemist as appropriate for the protection of the group in question and may be introduced by conventional methods Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned would be available to the skilled chemist and are within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include esters involving straight or branched chain $C_{1-12}$alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and $C_{2-6}$alkenyl groups (for example allyl and vinylethyl).

Methods particularly appropriate for the removal of carboxyl protecting groups include for example acid-, base-, metal- or enzymically-catalysed hydrolysis.

Examples of hydroxy protecting groups include ethers involving lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl groups (for example trimethylsilyl, tert-butyldimethylsilyl) and aryl lower alkyl groups (for example benzyl).

Examples of amino protecting groups include amides or amines involving formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

According to a further aspect of the present invention there is provided a compound of the Formula (I), or a pharmaceutically acceptable salt or an in vivo cleavable ester thereof as defined hereinbefore, for use in a method of treatment of the human or animal body by therapy.

In a further aspect of the present invention there is provided a compound of the Formula (I), or a pharmaceutically acceptable salt or an in vivo cleavable ester thereof as defined hereinbefore, for use as a medicament.

In a further aspect the present invention provides the use of a compound of the Formula (I), or a pharmaceutically acceptable salt or an in vivo cleavable ester thereof as defined hereinbefore, in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in inhibiting TNF.

In a further aspect the present invention provides a method of inhibiting TNF which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the. Formula (I), or a pharmaceutically acceptable salt or an in vivo cleavable ester thereof as defined hereinbefore, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula (I), or a pharmaceutically acceptable salt or an in vivo cleavable ester thereof as defined hereinbefore.

In a further aspect the present invention provides the use of a compound of the Formula (I), or a pharmaceutically acceptable salt or an in vivo cleavable ester thereof as defined hereinbefore, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis. AIDS, septic shock, congestive heart failure, ischaemic heart disease or psoriasis which comprises administering to a warm-blooded animal an effective amount of a compound of the Formula (I), or a pharmaceutically acceptable salt or an in vivo cleavable ester thereof as defined hereinbefore.

The following biological assays and Examples serve to illustrate the present invention.

Biological Assays

The following assays can be used to measure the p38 kinase-inhibitory, the TNF-inhibitory and anti-arthritic effects of the compounds of the present invention:

In Vitro Enzyme Assay

The ability of compounds of the invention to inhibit the enzyme p38 kinase was assessed. Activity of particular test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 $\mu$l of 10 mg/ml) or p38β (10 $\mu$l of 5 mg/ml) together with MKK6 (10 $\mu$l of 1 mg/ml), 'Kinase buffer' [100 $\mu$l; pH 7.4 buffer comprising Tris (50 mM), EGTA (0.1 mM), sodium orthovanadate (0.1 mM) and β-mercaptoethanol (0.1%)] and MgATP (30 $\mu$l of 50 mM Mg(OCOCH$_3$)$_2$ and 0.5 mM ATP). This produced enough activated p38 enzyme for 3 Microtiter plates.

Test compounds were solubilised in DMSO and 10 $\mu$l of a 1:10 diluted sample in 'Kinase Buffer' was added to a well in a Microtiter plate. For single dose testing, the compounds were tested at 10 $\mu$M. 'Kinase Assay Mix' [30 $\mu$l; comprising Myelin Basic Protein (Gibco BRL cat. no. 1322B-010; 1 ml of a 3.33 mg/ml solution in water), activated p38 enzyme (50 $\mu$l) and 'Kinase Buffer' (2 ml)] was then added followed by 'Labelled ATP' [10 $\mu$l; comprising 50 $\mu$M ATP, 0.1 $\mu$Ci $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 $\mu$l of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-Based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin 50 $\mu$g/ml streptomycin, 2 mM glutamine and 1% heat-inactivated human AB serum (Sigma H-1513)].

Compounds were solubilised in DMSO at a concentration of 50 mM, diluted 1:100 in culture medium and subsequently serial dilutions were made in culture medium containing 1% DMSO. PBMCs ($2.4 \times 10^5$ cells in 160 µl culture medium) were incubated with 20 µl of varying concentrations of test compound (triplicate cultures) or 20 µl culture medium containing 1% DMSO (control wells) for 30 minutes at 37° C. in a humidified (5% $CO_2$/95% air) incubator (Falcon 3072; 96 well flat-bottom tissue culture plates). 20 µl lipopolysaccharide [LPS *E. Coli* 0111:B4 (Sigma L-4130), final concentration 10 µg/ml] solubilised in culture medium was added to appropriate wells. 20 µl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 µl of the supernatant was removed from each well and stored at −70° C. (96 well round-bottom plates; Coming 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

$$\% \text{ inhibition} = \frac{(\text{LPS alone-medium alone}) - (\text{test concentration-medium alone})}{(\text{LPS alone-medium alone})} \times 100$$

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 µl whole blood were added to 96 well round-bottom plates (Corning 25850). Compounds were solubilised and serially diluted in RPMI 1640 medium (Gibco) supplemented with 50 units/ml penicillin, 50 µg/ml streptomycin and 2 mM glutamine, as detailed above. 20 µl of each test concentration was added to appropriate wells (triplicate cultures). 20 µl of RPMI 1640 medium supplemented with antibiotics and glutamine was added to control wells. Plates were incubated for 30 minutes at 37° C. (humidified incubator), prior to addition of 20 µl LPS (final concentration 10 µg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 µl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal(i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 µl of each sample was added to a set format pattern in a 96 well round bottom plate (Coming 25850). 50 µl of heparinized human blood was then added to each well, mixed and the plate was incubated for 30 min at 37° C. (humidified incubator). LPS (25 µl; final concentration 10 µg/ml) was added to the wells and incubation continued for a further 5.5 hours. Control wells were incubated with 25 µl of medium alone. Plates were then centrifuged for 10 min at 2000 rpm and 200 µl of the supernatants were transferred to a 96 well plate and frozen at −20° C. for subsequent analysis of TNF concentration by ELISA.

Data analysis by dedicated software calculates for each compound/dose:

$$\% \text{ inhibition of TNF}\alpha = \frac{\text{Mean TNF}\alpha(\text{Controls}) - \text{Mean TNF}\alpha(\text{Treated})}{\text{Mean TNF}\alpha(\text{Controls})} \times 100$$

Alternatively, mice could be used instead of rats in the above procedure.

Test as Anti-Arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146 857.
2. Williams, R. O. et al., (1992) *Proc. Natl. Acad. Sci.* 89, 9784.
3. Williams, R. O. et al., (1995) *Immunology*, 8, 433.
4 Badger, M. B. et al., (1996) *The Journal of Pharmacology and Experimental Therapeutics*, 279, 1453–1461.

Although the pharmacological properties of the compounds of the Formula (I) vary with structural change as expected, in general a compound of the Formula (I) gives over 30% inhibition of p38α and/or p38β at concentrations up to 10 µM and over 30% inhibition in the PBMC test at concentrations up to 50 µM. No physiologically unacceptable toxicity was observed at the effective dose for compounds tested of the present invention. By way of example:—

| Example | IC$_{50}$ (p38α) | IC$_{50}$ (PBMC) |
|---|---|---|
| 11 | 1.3 | 3.6 |
| 14 | 3.4 | 3.2 |
| 24 | 0.2 | 5.2 |
| 38 | 0.1 | 2 |

EXAMPLES

The invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) was performed on Merck Kieselgel silica Art. 9385) or Merck Lichroprep RP-18 (Art. 9303) reversed-phase silica obtained from E. Merck, Darmstadt, Germany, or high pressure liquid chromatography (HPLC) was performed on C18 reversed-phase silica, for example on a Dynamax C-18 60 Å preparative reversed-phase column;

(iv) yields where present are given for illustration only and are not necessarily the maximum attainable;

(v) in general, the end-products of the Formula (I) have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad; unless otherwise stated deuterated dimethyl sulphoxide (DMSO-d$_6$) was the solvent used;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:—

| | |
|---|---|
| DMF | N,N-dimethylformamide |
| DMSO | dimethylsulphoxide |
| DMA | N,N-dimethylacetamide. |
| THF | tetrahydrofuran |

Example 1

4-[3-(3-Methoxybenzamido)anilino]-6,7-dimethoxyquinazoline hydrochloride

3-Methoxybenzoyl chloride (0.169 ml) was added to a suspension of 4-(3-aminoanilino)-6,7-dimethoxyquinazoline (300 mg) in dry methylene chloride (10 ml). The reaction was stirred at ambient temperature for 18 hours. The precipitated solid was isolated, washed with methylene chloride and diethyl ether and then dried under vacuum to yield the title compound (398 mg, 85%); NMR: 3.84 (s, 3H), 3.98 (s, 3H), 4.02 (s, 3H), 7.15 (m, 1H), 7.35 (s, 1H), 7.4–7.56 (m, 5H), 7.66 (m, 1H), 8.21 (s, 1H), 8.31 (s, 1H), 8.8 (s, 1H), 10.41 (s, 1H), 11.38 (s, 1H); m/s: M+H$^+$ 431.

The 4-(3-aminoanilino)-6,7-dimethoxyquinazoline used as a starting material was prepared as follows:—

A mixture of 4,5-dimethoxyanthranilic acid (19.7 g) and formamide (10 ml) was stirred and heated to 190° C. for 5 hours. The mixture was allowed to cool to approximately 80° C. and water (50 ml) was added. The mixture was stored at ambient temperature for 3 hours. The precipitate was isolated, washed with water and dried to give 6,7-dimethoxy-3,4-dihydroquinazolin-4-one (3.65 g).

A mixture of 6,7-dimethoxy-3,4-dihydroquinazolin-4-one (2.06 g), thionyl chloride (20 ml) and DMF (1 drop) was stirred and heated to reflux for 2 hours. The mixture was evaporated and the residue was partitioned between ethyl acetate and a saturated aqueous sodium hydrogen carbonate solution. The organic phase was washed with water, dried over magnesium sulphate, filtered and evaporated to dryness. The residue was purified by column chromatography using increasingly polar mixtures of methylene chloride and ethyl acetate as the eluant to give 4-chloro-6,7-dimethoxyquinazoline (0.6 g, 27%).

3-Aminoaniline (4.79 g) was added to a suspension of 4-chloro-6,7-dimethoxyquinazoline (1.99 g) in isopropanol (100 ml). A 1M solution of hydrogen chloride in diethyl ether (8.86 ml) was added and the reaction mixture was stirred and heated to 90° C. for 3 hours. The mixture was cooled to ambient temperature and the precipitated solid was isolated, washed with isohexane and diethyl ether and then dried under vacuum. The resulting solid was then stirred with 1M aqueous sodium hydroxide solution and the mixture was extracted with methylene chloride. The methylene chloride extract was evaporated to dryness. There was thus obtained the required starting material (1.07 g, 41%); NMR: 3.91 (s, 3H), 3.93 (s, 3H), 5.03 (s, 2H), 6.31 (d, 1H), 6.87 (d, 1H), 7.00 (m, 2H), 7.13 (s, 1H), 7.81 (s, 1H), 8.39 (s, 1H), 9.20 (s, 1H); m/s: M+H$^+$ 297.

Example 2

4-[4-Chloro-3-(3,4-dimethoxybenzamido)anilino]-6,7-dimethoxyquinazoline hydrochloride 3,4-Dimethoxybenzoyl chloride (200 mg) and triethylamine (0.125 ml) were added to a suspension of 4-(3- amino-4-chloroanilino)-6,7-dimethoxyquinazoline (150 mg) in dry methylene chloride (3 ml) and the mixture was stirred at ambient temperature for 18 hours. The reaction mixture was diluted with methylene chloride and washed with water and brine and evaporated. The residue was triturated with diethyl ether (3×100 ml). The resulting solid was stirred in ethereal hydrogen chloride at ambient temperature for 18 hours and the mixture was evaporated to dryness. The resulting solid was triturated with isohexane and dried under vacuum. The title compound was obtained as a solid (30 mg); NMR: 3.85 (s, 6H), 3.92 (s, 3H), 3.96 (s, 3H), 6.98 (m, 1H), 7.32 (s, 1H), 7.45 (m, 2H), 7.99 (m, 1H), 8.15 (s, 1H), 8.88 (s, 1H), 9.98 (s, 1H), 11.32 (s, 1H); m/s: M+H$^+$ 495, 497.

The 4-(3-amino-4-chloroanilino)-6,7-dimethoxyquinazoline used as a starting material was prepared as follows:—

Concentrated hydrochloric acid (2.5 ml) was added to a mixture of 4-chloro-6,7-dimethoxyquinazoline (3.0 g) and 4-chloro-3-nitroaniline (2.54 g) in isopropanol (100 ml) and stirred and heated to 85° C. for 18 hours. After cooling the precipitated solid was isolated and washed with isohexane and diethyl ether. There was thus obtained 4-(4-chloro-3-nitroanilino)-6,7-dimethoxyquinazoline hydrochloride as a solid (4.65 g, 87%); NMR: 3.99 (s, 3H), 4.06 (s, 3H), 7.38 (m, 1H), 7.85 (m, 1H), 8.22 (m, 1H), 8.49 (m, 1H), 8.63 (m, 1H), 8.92 (m, 1H), 11.83 (s, 1H); m/s: M+H$^+$ 361, 363.

Iron powder (3.39 g) was added to a stirred mixture of 4-(4-chloro-3-nitroanilino)-6,7-dimethoxyquinazoline hydrochloride (4.37 g) in water (200 ml) and glacial acetic acid (2 ml) and heated to 110° C. for 4.5 hours. After cooling ethyl acetate (200 ml) was added and the mixture was filtered through diatomaceous earth (Celite®). The organic layer was separated and evaporated to dryness. This solid was partitioned between methylene chloride and water. The organic layer was then washed with brine dried over sodium sulphate, filtered and evaporated to dryness to yield the required starting material (1.15 g, 29%); NMR: 3.91 (s, 3H), 3.93 (s, 3H), 5.32 (s, 2H), 6.95 (m, 1H), 7.15 (m, 2H), 7.3 (m, 1H), 7.8 (s, 1H), 8.42 (s, 1H); 9.28 (s, 1H); m/s: M+H$^+$ 331, 333.

Example 3

4-(2-Fluoro-4-chloro-5-benzamidoanilino)-6,7-dimethoxyquinazoline hydrochloride Benzoyl chloride (0.025 ml) and pyridine (0.036 ml) were added to a suspension of 4-(5-amino-4-chloro-2-fluoroanilino)-6,7-dimethoxyquinazoline (125 mg) in dry methylene chloride (3 ml) and the resulting mixture was stirred at ambient temperature for 18 hours. Isohexane (3 ml) was added and the precipitated solid was isolated, washed with diethyl ether and dried under vacuum. The title compound was obtained as a solid (65 mg); NMR: 4.0 (s, 6H), 7.35 (s, 1H), 7.56 (m, 3H), 7.78 (d, 2H), 7.99 (d, 2H), 8.22 (s 1H), 8.81 (s, 1H), 10.2 (broad s, 1H); m/s: M+H$^+$ 453, 455.

The 4-(5-amino-4-chloro-2-fluoroanilino)-6,7-dimethoxyquinazoline used as a starting material was prepared as follows:—

Phthalic anhydride (11.83 g) was added to a solution of 2-chloro-4-fluoroaniline (11.08 g) in glacial acetic acid (150 ml). The resulting mixture was heated to 100° C. for 2 hours then allowed to cool. The precipitated solid was isolated, washed with water and dried under vacuum. The solid thus obtained was suspended in sulphuric acid (30 ml) and a mixture of nitric acid (4.6 ml) and sulphuric acid (5 ml) was added gradually with cooling in an ice-water bath, such that the internal reaction temperature did not exceed 30° C. The resulting clear solution was stirred at ambient temperature for 1 hour. Ice-water (250 ml) was added and the precipitated solid was isolated and dried under vacuum. There was thus obtained N-(2-chloro-4-fluoro-5-nitrophenyl)phthalimide as a solid (17.9 g, 73%); NMR: (CDCl$_3$): 7.58 (d, 1H), 7.88 (m, 2H), 8.01 (m, 2H), 8.16 (d, 1H); m/s: [M–H]$^-$ 319, 321.

A mixture of ethanol (450 ml), water (65 ml) and acetic acid (6.5 ml) was heated to 50° C. with stirring. Iron powder (9.0 g) was added followed by N-(2-chloro-4-fluoro-5-nitrophenyl)phthalimide (8.98 g) portionwise over 10 minutes. The resulting mixture was stirred and heated to reflux for 2 hours. After cooling, solid sodium carbonate was added with stirring until effervescence ceased. The resulting mixture was filtered through diatomaceous earth (Celite®) washing with ethanol. The filtrate was evaporated and the residue partitioned between methylene chloride and saturated aqueous sodium bicarbonate solution. The organic extract was washed with brine, dried over sodium sulphate, filtered and evaporated to dryness. There was thus obtained N-(5-amino-2-chloro-4-fluorophenyl)phthalimide as a solid; NMR (CDCl$_3$): 3.87 (s, 2H), 6.74 (d, 1H), 7.2 (d, 1H), 7.81 (m, 2H), 7.96 (m, 2H), m/s: [M–H]$^-$ 289, 291.

N-(5-Amino-2-chloro-4-fluorophenyl)phthalimide (957 mg) was added to a suspension of 4-chloro-6,7-dimethoxyquinazoline (674 mg) in isopropanol (25 ml). A 1M solution of hydrogen chloride in diethyl ether (3.0 ml) was added and the reaction mixture stirred and heated to 85° C. for 3 hours. After cooling the precipitated solid was isolated and washed with isohexane and diethyl ether. There was thus obtained 4-(4-chloro-2-fluoro-5-phthalimidoanilino)-6,7-dimethoxyquinazoline hydrochloride as a solid (1.21 g, 84%); NMR: 4.0 (s, 6H), 7.35 (s, 1H), 7.9 (d, 1H), 7.96 (m, 3H), 8.02 (m, 2H), 8.19 (s, 1H), 8.96 (s, 1H); m/s: M+H$^+$ 479, 481.

4-(4-Chloro-2-fluoro-5-phthalimidoanilino)-6,7-dimethoxyquinazoline hydrochloride (1.06 g) was dissolved in ethanolamine (10 ml) and the resulting mixture was stirred at ambient temperature for 20 minutes. The mixture was dissolved in methylene chloride (200 ml) and the resulting solution washed with water and brine, dried over sodium sulphate, filtered and evaporated to dryness. There was thus obtained 4-(5-amino-4-chloro-2-fluoroanilino)-6,7-dimethoxyquinazoline as a solid (701 mg, 91%); NMR: 3.96 (s, 6H), 5.23 (s, 2H), 6.94 (d, 1H), 7.17 (s, 1H), 7.23 (d, 1H), 7.76 (s, 1H), 8.33 (s, 1H), 9.33 (s, 1H); m/s: M+H$^+$ 349, 351.

Examples 4–23

Using an analogous procedure to that described in Example 1, the appropriate acyl chloride was reacted with the appropriate aniline to give, unless otherwise stated in the appropriate footnote, the hydrochloride salt of each compound described in the following table.

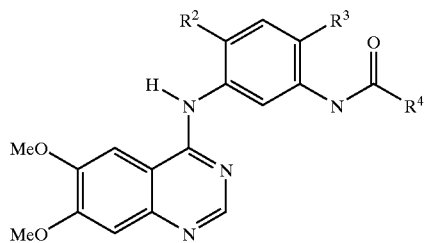

| Example No. | R² | R³ | R⁴ | Note |
|---|---|---|---|---|
| 4 | H | H | 3-fluorophenyl | a) |
| 5 | H | H | 2-tolyl | b) |
| 6 | H | F | phenyl | c) |
| 7 | H | F | 4-cyanophenyl | d) |
| 8 | H | F | 3-dimethylaminophenyl | e) |
| 9 | H | Cl | 4-cyanophenyl | f) |
| 10 | H | Cl | 3-dimethylaminophenyl | g) |
| 11 | H | Me | phenyl | h) |
| 12 | F | Cl | 3-dimethylaminophenyl | i) |
| 13 | H | F | methyl | j) |
| 14 | H | F | ethyl | k) |
| 15 | H | Cl | methyl | l) |
| 16 | H | Cl | ethyl | m) |
| 17 | F | Cl | methyl | n) |
| 18 | H | F | methoxymethyl | o) |
| 19 | H | Cl | methoxymethyl | p) |
| 20 | F | Cl | 4-cyanophenyl | q) |
| 21 | H | H | 2-furyl | r) |
| 22 | H | H | 6-chloropyrid-3-yl | s) |
| 23 | Me | H | 5-isoxazolyl | t) |

Notes a) The product gave the following data: NMR: 3.98(s, 3H), 4.02(s, 3H), 7.35(s, 1H), 7.45(m, 3H), 7.6(m, 2H), 7.83(m, 2H) 8.21(s, 1H), 8.31(s, 1H), 8.8(s, 1H), 10.52(s, 1H), 11.36(s, IH); Mass: M + H⁺419.

b) The product gave the following data: NMR: 2.38(s, 3H), 3.99(s, 3H), 4.01 (s, 3H), 7.28(m, 2H), 7.35–7.48(m, 5H), 7.55(m, 1H), 8.17(s, 1H), 8.28(s, 1H), 8.78(s, 1H), 10.46(s, 1H); Mass: M + H⁺ 415.

c) The product gave the following data: NMR: 3.95(s, 3H), 4.0(s, 3H), 7.35–7.65(m, 6H), 8.0(m, 3H), 8.35(s, 1H), 9.02(s, 1H), 10.26(s, 1H), 11.51(s, 1H); Mass: M + H⁺ 419.

The 4-(3-amino-4-fluoroanilino-6,7-dimethoxyquinazoline used as a starting material was prepared as follows:

Using analogous procedures to those described in the portion of Example 2 which is concerned with the preparation of starting materials, 4-chloro-6,7-dimethoxyquinazoline was reacted with 4-fluoro-3-nitroaniline to give 4-(4-fluoro-3-nitroanilino)-6,7-dimethoxyquinazoline hydrochloride; NMR: 3.98(s, 3H), 4.03(s, 3H), 7.39(m, 1H), 7.7(m, 1H), 8.25(m, 1H), 8.44(m, 1H), 8.62(m, 1H), 8.9(m, 1H), 11.85(s, 1H); Mass:M + H⁺ 345 and that material was reduced during 1.5 hours to give 4-(3-amino-4-fluoroanilino)-6,7-dimethoxyquinazoline; NMR: 3.9(s, 3H), 3.92(s, 3H), 5.11(s, 2H), 6.84 (m, 1H), 6.96(m, 1H), 7.12(s, 1H), 7.18(s, 1H), 7.79(s, 1H), 8.39(s, 1H); 9.22(s, 1H); Mass: M + H⁺ 315.

d) The product gave the following data: NMR: 3.99(s, 3H), 4.01(s, 3H), 7.36(s, 1H), 7.42(m, 1H), 7.61(m, 1H), 8.0(m, 3H), 8.14(m, 2H), 8.36(s, 1H), 8.81(s, 1H), 10.57(s, 1H), 11.54(s, 1H); Mass: M + H⁺ 444.

e) The product was obtained as a dihydrochloride salt and gave the following data: NMR: (DMSOd₆ + CD₃CO₂D): 3.04(s, 6H), 3.98(s, 3H), 4.0(s, 3H), 7.36(s, 1H), 7.25–7.5(m, 3H), 7.55(m, 1H), 7.67(m, 1H), 8.0 (m, 1H), 8.23(s, 1H); 8.8(s, 1H); Mass: M + H⁺ 462.

f) The product gave the following data: NMR: 3.98(s, 3H), 4.0(s, 3H), 7.38(s, 1H), 7.66(m, 1H), 7.75(m, 1H), 8.02(m, 3H), 8.14(m, 2H), 8.38(s, 1H), 8.85(s, 1H), 10.5(s, 1H), 11.55(s, 1H); Mass: M + H⁺ 460 & 462.

g) The product was obtained as a dihydrochioride salt and gave the following data: NMR: (DMSOd₆ + CD₃CO₂D): 3.05(s, 6H), 3.97(s, 3H), 3.99(s, 3H), 7.25–7.8(m, 7H), 8.04(m, 1H), 8.31(m, 1H), 8.85(s, 1H); Mass: M + H⁺ 478 & 480.

h) The product gave the following data: NMR: 2.14 (s, 3H), 3.98(s, 3H), 4.0(s, 3H), 7.36(m, 2H), 7.52(m, 4H), 7.73(m, 1H), 7.99(m, 2H), 8.31(s, 1H), 8.79(s, 1H), 9.98(s, 1H), 11.38(s, 1H); Mass: M + H⁺ 415.

The 4-(3-amino-4-methylanilino)-6,7-dimethoxyquinazoline used as a starting material was prepared as follows:

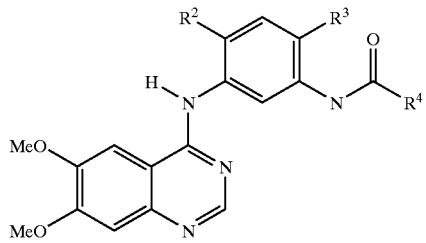

| Example No. | R² | R³ | R⁴ | Note |
|---|---|---|---|---|

Using analogous procedures to those described in the portion of Example 2 which is concerned with the preparation of starting materials, 4-chloro-6,7-dimethoxyquinazoline was reacted with 4-methyl-3-nitroaniline to give 4-(4-methyl-3-nitroanilino)-6,7-dimethoxyquinazoline hydrochloride; NMR: 2.54(s, 3H), 3.98(s, 3H), 4.02(s, 3H), 7.38(s, 1H), 7.58(m, 1H), 8.06(m, 1H), 8.43(m, 2H), 8.89(s, 1H), 11.72(s, 1H); Mass:M + H⁺ 341 and that material was reduced during 5 hours to give 4-(3-amino-4-methylanilino)-6,7-dimethoxyquinazoline; NMR: 2.04(s, 3H), 3.9(s, 3H), 3.92(s, 3H), 4.88(s, 2H), 6.8 (m, 1H), 6.9(m, 1H), 7.03(s, 1H), 7.12(m, 1H), 7.8(s, 1H), 8.38(s, 1H); 9.2(s, 1H); Mass: M + H⁺ 311.

i) The product was obtained as a dihydrochloride salt and gave the following data: NMR: 2.99(s, 6H), 4.0(s, 6H), 7.4(m, 5H), 7.76(m, 2H), 8.4(s, 1H), 8.84(s, 1H), 10.22(s, 1H), 11.89(s, 1H); Mass: M + H⁺ 496 & 498.

j) The product gave the following data: NMR: 2.1(s, 3H), 3.98(s, 3H), 4.0(s, 3H), 7.32(m, 2H), 7.42(m, 1H), 8.0(m, 1H), 8.26(s, 1H), 8.99(s, 1H), 9.88(s, 1H), 11.36(s, 1H); Mass: M + H⁺ 357.

k) The product gave the following data: NMR: 1.05(t, 3H), 2.4(q, 2H), 3.97(s, 3H), 3.99(s, 3H), 7.35(m, 2H), 7.42(m, 1H), 8.2(m, 1H), 8.3(s, 1H), 8.79(s, 1H), 9.78(s, 1H), 11.41(s, 1H); Mass: M + H⁺ 371.

l) The product gave the following data: NMR: 2.10(s, 3H), 3.99(s, 3H), 3.97(s, 3H), 7.34(m, 1H), 7.58(m, 2H), 8.07(m, 1H), 8.27(s, 1H), 8.81(s, 1H), 9.61(s, 1H), 11.33(s, 1H); Mass: M + H⁺ 373 & 375.

m) The product gave the following data: NMR: 1.05(t, 3H), 2.4(q, 2H), 3.97(s, 3H), 3.99(s, 3H), 7.35(s, 1H), 7.58(m, 2H), 8.05(m, 1H), 8.29(s, 1H), 8.82(s, 1H), 9.53(s, 1H), 11.4(s, 1H); Mass: M + H⁺ 387 & 389.

n) The product gave the following data: NMR: 2.08(s, 3H), 4.0(s, 6H), 7.35(s, 1H), 7.69(d, 1H), 7.86(d, 1H), 8.23(s, 1H), 8.79(s, 1H), 9.67(s, 1H), 11.52(broad s, 1H); Mass: M + H⁺ 391 & 393.

o) The product gave the following data: NMR: 3.40(s, 3H), 3.98(s, 3H), 4.0(s, 3H), 4.06(s, 2H), 7.35(s, 1H), 7.4(m, 1H), 7.5(m, 1H), 8.13(m, 1H), 8.3(s, 1H), 8.79(s, 1H), 9.57(s, 1H), 11.43(s, 1H); Mass: M + H⁺ 387.

p) The product gave the following data: NMR: 3.44(s, 3H), 3.99(s, 3H), 4.01(s, 3H), 4.05(s, 2H), 7.36(s, 1H), 7.6(m, 2H), 8.3(m, 2H), 8.82(s, 1H), 9.35(s, 1H), 11.43(s, 1H); Mass: M + H⁺ 403 & 405.

q) An analogous procedure to that described in Example 3 was used. The product gave the following data: NMR: 4.0(s, 6H), 7.35(s, 1H), 7.77(d, 1H), 7.82(d, 1H), 8.03(d, 2H), 8.14(d, 2H), 8.26(s, 1H), 8.81(s, 1H), 10.52 (s, 1H); Mass: M + H⁺ 478 & 480.

r) The product gave the following data: NMR: 3.99(s, 3H), 4.01(s, 3H), 7.68(m, 1H), 7.37(s, 1H), 7.4(m, 3H), 7.62(d, 1H), 7.92(s, 1H), 8.16(s, 1H), 8.27(s, 1H), 8.79(s, 1H), 10.37(broad s, 1H), 11.35(broad s, 1H); Mass: M + H⁺ 391.

s) The product gave the following data: NMR: 3.99(s, 3H), 4.01(s, 3H), 7.35(s, 1H), 7.44(m, 1H), 7.63(m, 1H), 7.65(d, 1H), 8.19(s, 1H), 8.29(s, 1H), 8.38(dd, 1H), 8.78(s, 1H), 8.96(s, 1H), 10.53(broad s, 1H), 11.37 (broad s, 1H); Mass: M + H⁺ 436 & 438.

t) The product gave the following data: NMR: 2.16(s, 3H), 3.98(s, 6H), 7.32(m, 3H), 7.66(d, 1H), 7.84(s, 1H), 8.27(s, 1H), 8.69(s, 1H), 8.78(s, 1H), 10.91(broad s, 1H), 11.44(broad s, 1H); Mass: M + H⁺ 406.

The 4-(5-amino-2-methylanilino)-6,7-dimethoxyquinazoline used as a starting material was prepared as follows:

Using analogous procedures to those described in the portion of Example 2 which is concerned with the preparation of starting materials, 4-chloro-6,7-dimethoxyquinazoline was reacted with 2-methyl-5-nitroaniline to give 4-(2-methyl-5-nitroanilino)-6,7-dimethoxyquinazoline hydrochloride; Mass: M + H⁺ 341 and that material was reduced during 5 hours to give 4-(5-amino-2-methylanilino)-6,7-dimethoxyquinazoline; Mass: M + H⁺ 311.

Example 24

4-[2-Methyl-5-(3-dimethylaminobenzamido) anilino]-6,7,8-trimethoxyquinazoline

3-Dimethylaminobenzoyl chloride (105 mg) was added to a suspension of 4-(2-methyl-5-aminoanilino)-6,7,8-trimethoxyquinazoline (180 mg) in dry methylene chloride (4 ml) and the resulting mixture was stirred at ambient temperature for 18 hours. Methylene chloride (100 ml) was added and the mixture washed with aqueous sodium hydroxide solution (100 ml), water and brine, dried over sodium sulphate, filtered and evaporated give a yellow gum. This was purified by silica column chromatography, eluting with 2% methanol in methylene chloride to yield the title compound as a solid (30 mg, 12%); NMR (CDCl$_3$) 2.22 (s, 3H), 2.97 (s, 6H), 3.96 (s, 3H), 4.06 (s, 3H), 4.13 (s, 3H), 6.84 (dd, 1H), 7.05 (m, 2H), 7.18 (m, 2H), 7.28 (t, 1H), 7.42 (m, 1H), 7.92 (s, 1H), 7.95 (s, 1H), 8.61 (s, 1H); m/s: M+H$^+$ 488.

The 3-dimethylaminobenzoyl chloride hydrochloride used as a starting material was prepared as follows:—

Oxalyl chloride (0.58 ml) was added to a stirred solution of 3-dimethylaminobenzoic acid (1.0 g) in methylene chloride (30 ml) followed by dimethylformamide (30 ml). The reaction was stirred at ambient temperature for 1 hour and then evaporated to dryness. There was thus obtained the required compound as a solid (1.33 g, quantitative); NMR: (CDCl$_3$) 3.25 (s, 6H), 7.75 (t, 1H), 8.27 (d, 1H), 8.39 (m, 2H).

The 4-(5-amino-2-methylanilino)-6,7,8-trimethoxyquinazoline used as a starting material was prepared as follows:—

2-Methyl-5-nitroaniline (0.711 g) was added to a suspension of 4-chloro-6,7,8-trimethoxyquinazoline hydrochloride (JP 10175972 A2; 1.1 g) in isopropanol (40 ml) and the resultant solution heated to 80° C. and stirred for 18 hours. The reaction mixture was evaporated, then partitioned between methylene chloride and 2M aqueous sodium hydroxide solution, the organic phases were washed with water and brine, dried (Na$_2$SO$_4$) and evaporated give a yellow solid. This was purified by silica column chromatography, eluting with 2.5% methanol in methylene chloride There was thus obtained 4-(2-methyl-5-nitroanilino)-6,7,8-trimethoxyquinazoline as a solid (662 mg, 45%); NMR: 2.32 (s, 3H), 3.9 (s, 3H), 3.95 (s, 3H), 4.0 (s, 3H), 7.59 (d, 1H), 7.66 (s, 1H), 8.06 (m, 1H), 8.2 (s, 1H), 8.36 (s, 1H), 9.62 (s, 1H); m/s: M+H$^+$ 371.

Using similar procedures to those described in the last paragraph of the portion of Example 2 which is concerned with the preparation of starting materials, a solution of 4-(2-methyl-5-nitroanilino)-6,7,8-trimethoxyquinazoline in a 30:3:1 mixture of ethanol, acetic acid and water was reduced at 90° C. during 18 hours. Solid sodium carbonate was added after cooling. The filtrate was triturated with diethyl ether and the resultant residue was purified by column chromatography eluting with 2.5% methanol in ethyl acetate to give 4-(5-amino-2-methylanilino)-6,7-dimethoxyquinazoline; NMR: (CDCl$_3$) 2.73 (s, 3H), 3.95 (s, 3H), 4.04 (s, 3H), 4.14 (s, 3H), 6.9 (s, 1H), 7.21 (m, 2H), 7.64 (s, 1H), 7.96 (d, 1H), 8.50 (s, 1H), 8.72 (s, 1H); Mass: M+H$^+$ 341.

Example 25

4-[4-Fluoro-3-(methoxycarbonylamino)anilino]-6,7-dimethoxyquinazoline

Methyl chloroformate (0.048 ml) was added to a suspension of 4-(3-amino-4-fluoroanilino)-6,7-dimethoxyquinazoline (161 mg) and triethylamine (0.14 ml) in dry methylene chloride (3.5 ml) and the resulting mixture was stirred at ambient temperature for 18 hours. Methylene chloride (100 ml) was added and the mixture washed with water and brine, dried over magnesium sulphate, filtered and evaporated to dryness. The residue was purified by silica column chromatography, eluting with 3% methanol in methylene chloride to yield the title compound as a solid (16 mg, 8.4%); NMR: 3.66 (s, 3H), 3.92 (s, 3H), 3.96 (s, 3H), 7.16 (s, 1H), 7.22 (t, 1H), 7.57 (m, 1H), 7.82 (s, 1H), 8.01 (m, 1H), 8.42 (s, 1H), 9.34 (s, 1H), 9.47 (s, 1H); m/s: M+H$^+$ 373.

Example 26

4-[3-(4-Cyanobenzamido)anilino]-6,7-dimethoxyquinazoline hydrochloride

4-Chloro-6,7-dimethoxyquinazoline (225 mg) was added to 3-(4-cyanobenzamido)aniline (261 mg) in isopropanol (8 ml). A 1M solution of hydrogen chloride in diethyl ether (1.0 ml) was added and the reaction mixture stirred and heated to 85° C. for 18 hours. After cooling to room temperature the precipitated solid was isolated and washed with isohexane and diethyl ether. The title compound was obtained as a solid (399 mg); NMR: 3.99 (s, 3H), 4.01 (s, 3H), 7.37 (s, 1H), 7.45 (m, 2H), 7.65 (m, 1H), 8.02 (m, 2H), 8.12 (m, 2H), 8.20 (m, 1H), 8.31 (s, 2H), 8.80 (s, 1H), 10.71 (s, 1H), 11.44 (s, 1H); m/s: M+H$^+$ 426.

The 3-(4-cyanobenzamido)aniline used as a starting material was prepared as follows:—

4-Cyanobenzoyl chloride (1.0 g) in methylene chloride (20 ml) was added dropwise into an ice-cooled solution of m-phenylenediamine (3.24 g) and triethylamine (0.84 ml) in methylene chloride (100 ml). The reaction was allowed to stir at ambient temperature for 1 hour. The precipitate was filtered and washed with diethyl ether. The title compound was obtained as a solid (1.0 g, 70%); NMR: 5.00–5.15 (broad s, 2H), 6.31 (m, 1H), 6.84 (m, 1H), 6.95 (m, 1H), 7.8 (m, 1H), 7.97 (m, 2H), 8.03 (m, 2H), −10.14 (s, 1H); m/s: M+H$^+$ 238.

Example 27

4-(3-Benzamido-4-fluoroanilino)-6-methoxy-7-(3-morpholilopropoxy)quinazoline

4-Pentafluorophenoxy-6-methoxy-7-(3-morpholinopropoxy)quinazoline (242 mg) was added to a solution of 3-benzamido-4-fluoroaniline (126 mg) in isopropanol (5 ml). A 1M solution of hydrogen chloride in diethyl ether (1.0 ml) was added and the reaction mixture stirred and heated to 85° C. for 24 hours. After cooling to room temperature the precipitated solid was isolated and washed with isohexane and diethyl ether. The solid thus obtained was partitioned between 1M aqueous sodium hydroxide solution and methylene chloride. The organic phase was washed with brine, dried over magnesium sulphate, filtered and evaporated to dryness. The title compound was obtained (110 mg, 41%); NMR: 1.94 (m, 2H), 2.37 (m, 4H), 2.44 (t, 2H), 3.56 (m, 4H), 3.95 (s, 3H), 4.18 (t, 2H), 7.16 (s, 1H), 7.30 (dd, 1H), 7.56 (m, 3H), 7.72 (m, 1H), 7.84 (s, 1H), 8.0 (d, 2H), 8.04 (m, 1H), 8.43 (s, 1H), 9.5 (s, 1H), 10.14 (s, 1H); m/s: M+H$^+$ 532.

4-(3-Chloropropyl)morpholine used as an intermediate was prepared as follows:—

Morpholine (52.2 ml) and 1-bromo-3-chloropropane (30 ml) were taken up in dry toluene (180 ml) and stirred and heated to 70° C. for 3 hours. The resultant precipitate was filtered off and the filtrate evaporated to give an orange oil which was purified by vacuum distillation collecting fractions at 62° C./5 mmHg and 58° C./2 mmHg. The required compound was obtained as an oil (37.9 g, 77%); NMR: 1.85 (m, 2H), 2.3 (t, 4H), 2.38 (t, 2H), 3.53 (t, 4H), 3.65 (t, 2H); M/s: M+H+ 164.

The 4-pentafluorophenoxy-6-methoxy-7-(3-morpholinopropoxy)quinazoline used as a starting material was prepared as follows:—

A mixture of 2-amino-4-benzyloxy-5-methoxybenzaamide (J. Med. Chem. 1977, vol 20, 146–149, 10 g) and Gold's reagent (7.4 g) in dioxane (100 ml) was stirred and heated at reflux for 24 hours. Sodium acetate (3.02 g) and acetic acid (1.65 ml) were added to the reaction mixture and it was heated for a further 3 hours. The mixture was evaporated to dryness, water was added to the residue and the solid was filtered off, washed with water and dried. Recrystallization from acetic acid gave 7-benzyloxy-6-methoxy-3,4-dihydroquinazolin-4-one (8.7 g, 84%).

7-Benzyloxy-6-methoxy-3,4-dihydroquinazolin-4-one (10.1 g) was suspended in thionyl chloride (200 ml) then dimethylformamide (0.5 ml) added and the resultant mixture heated to 80° C. and stirred for 3 hours. The reaction mixture was evaporated and azeotroped with toluene to yield 4-chloro-7-hydroxy-6-methoxyquinazoline as a solid (12.1 g, 100%); NMR: 4.88 (s, 3H), 5.25 (s, 2H), 7.44 (s, 1H), 7.49 (s, 1H), 7.32–7.52 (m, 5H), 8.83 (s, 1H); m/s: M+H+ 283.

Potassium carbonate (17.2 g) was added to a suspension of 4-chloro-7-hydroxy-6-methoxyquinazoline (12.0 g) and 2,3,4,5,6-pentafluorophenol (7.88 g) in dimethylformamide (150 ml). The resultant mixture was stirred and heated to 100° C. for 18 hours. The mixture was evaporated and the residue partitioned between water and ethyl acetate, the organic phase was washed with brine, dried over magnesium sulphate, filtered and evaporated to dryness to yield 7-benzyloxy-6-methoxy-4-pentafluorophenoxyquinazoline as a solid (14.6 g, 89%); NMR (CDCl$_3$) 4.08 (s, 3H), 5.35 (s, 2H), 7.4 (s, 1H), 7.52 (s, 1H), 7.32–7.52 (m, 5H), 8.56 (s, 1H); m/s: M+H+ 449.

A solution of 7-benzyloxy-6-methoxy-4-pentafluorophenoxyquinazoline (14.6 g) in trifluoroacetic acid (100 ml) was heated to 70° C. and stirred for 1 hour. The mixture was evaporated to dryness, taken up in saturated aqueous sodium bicarbonate solution and stirred for 30 minutes. It was then filtered, washed with water and dried under vacuum at 40° C. overnight to yield 7-hydroxy-6-methoxy-4-pentafluorophenoxyquinazoline as a solid (11.6 g, 99%); NMR: 3.99 (s, 3H), 7.28 (s, 1H), 7.56 (s, 1H), 8.52 (s, 1H) 11.0 (s, 1H); m/s: M+H+ 359.

Potassium carbonate (12.5 g) was added to a suspension of 7-hydroxy-6-methoxy-4-pentafluorophenoxyquinazoline (7.73 g) and 4-(3-chloropropyl)morpholine (4.28 g) in dimethylformamide (180 ml). The resultant mixture was stirred and heated to 100° C. for 4 hours. After cooling to room temperature, the inorganic solids were filtered off and the filtrate was evaporated and the residue was partitioned between water and ethyl acetate, the organic phases were washed with brine, dried over magnesium sulphate, filtered and evaporated to dryness to yield 4-pentafluorophenoxy-6-methoxy-7-(3-morpholinopropoxy)quinazoline as a solid (9.37 g, 89%); NMR: 1.98 (m, 2H), 2.38 (m, 4H), 2.42 (t, 2H), 3.55 (t, 4H), 3.99 (s, 3H), 4.28 (t, 2H), 7.45 (s, 1H), 7.56 (s, 1H), 8.6 (s, 1H); m/s: M+H+ 486.

The 3-benzamido-4-fluoroaniline (alternatively named as N-(5-amino-2-fluorophenyl)benzamide) used as a starting material was prepared as follows:—

Triethylamine (5.85 ml) was added to a an ice-cooled solution of 2-fluoro-5-nitroaniline (3.9 g) in dry methylene chloride under an argon atmosphere. Benzoyl chloride (4.18 ml) was added gradually. The resulting mixture was stirred at ambient temperature for 18 hours. The reaction mixture was partitioned between water and methylene chloride, the organic phase was washed with saturated aqueous sodium bicarbonate solution and brine, dried over magnesium sulphate, filtered and evaporated to dryness to give a sticky solid. Trituration with hot isohexane and diethyl ether gave N-(2-fluoro-5-nitrophenyl)benzamide as a solid (3.2 g, 49%); NMR (CDCl$_3$) 7.26 (dd, 1H), 7.6 (m, 3H), 7.91 (d, 2H), 8.03 (m, 1H), 8.15 (broad s, 1H), 9.48 (dd, 1H); m/s: M+H+ 261.

N-(2-Fluoro-5-nitrophenyl)benzamide (3.2 g) was dissolved in methanol (250 ml) under an argon atmosphere. 10% palladium on activated carbon (250 mg) was added and the argon atmosphere replaced with hydrogen. The reaction mixture was stirred at ambient temperature until the requisite volume of hydrogen gas was taken up. The catalyst was removed by filtration and the filtrate evaporated to give the required compound as white solid (2.66 g, 94%); NMR: (CDCl$_3$) 3.64 (broad s, 2H), 6.36 (m, 1H), 6.92 (dd, 1H), 7.53 (m, 3H), 7.87 (d, 2H), 7.93 (dd, 1H), 8.01 (broad s, 1H); m/s: M+H+ 231.

Examples 28–45

Using an analogous procedure to that described in Example 26 or 27, the appropriate 4-chloro or 4-pentafluorophenoxyquinazoline was reacted with the appropriate aniline to give the compounds described in the following table. Unless otherwise stated, each compound prepared by the method of Example 26 were obtained as the hydrochloride salt. In the preparation of each compound by the method of Example 27, the step of treatment with 1M aqueous sodium hydroxide was omitted and each such product was obtained as a dihydrochloride salt.

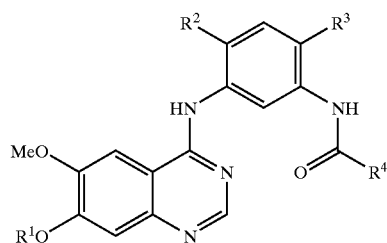

| Ex. No | R¹ | R² | R³ | R⁴ | Method | Note |
|---|---|---|---|---|---|---|
| 28 | Me | H | H | 3-dimethylaminophenyl | Ex. 26 | a) |
| 29 | Me | Me | H | phenyl | Ex. 26 | b) |
| 30 | Me | Cl | H | phenyl | Ex. 26 | c) |
| 31 | Me | Me | H | 4-cyanophenyl | Ex. 26 | d) |
| 32 | Me | Cl | H | 4-cyanophenyl | Ex. 26 | e) |
| 33 | Me | Me | H | 3-dimethylaminophenyl | Ex. 26 | f) |
| 34 | Me | Cl | H | 3-dimethylaminophenyl | Ex. 26 | g) |
| 35 | Me | Me | H | 3,4-dimethoxyphenyl | Ex. 26 | h) |
| 36 | Me | F | F | phenyl | Ex. 26 | i) |
| 37 | Me | Cl | F | 3-dimethylaminophenyl | Ex. 26 | j) |
| 38 | 3-morpholinopropyl | Me | H | 3-dimethylaminophenyl | Ex. 26 | k) |
| 39 | Me | Cl | F | methoxymethyl | Ex. 26 | l) |
| 40 | 3-pyrid-3-ylpropyl | H | F | methoxymethyl | Ex. 27 | m) |
| 41 | 3-morpholinopropyl | H | F | methoxymethyl | Ex. 27 | n) |
| 42 | 2-morpholinoethyl | H | F | methoxymethyl | Ex. 27 | o) |
| 43 | 2-pyrrolidin-1-ylethyl | H | F | methoxymethyl | Ex. 27 | p) |
| 44 | Me | Me | H | 3-morpholinophenyl | Ex. 26 | q) |
| 45 | Me | Me | H | 2-morpholinopyrid-4-yl | Ex. 26 | r) |

Notes a) The product gave the following data: NMR: 3.0(s, 6H), 3.98(s, 3H), 4.0(s, 3H), 7.2–7.6(broad m, 7H), 7.69(m, 2H), 8.2(m, 1H), 8.38(s, 1H), 8.8(s, 1H), 10.5(s, 1H), 11.55(s, 1H); Mass: M + H⁺ 444.
The N-(3-aminophenyl)-3-dimethylaminobenzamide used as a starting material was prepared as follows:
3-Nitroaniline (3.84 g) in methylene chloride (50 ml) was added dropwise to an ice-cooled solution of 3-dimethylaminobenzoyl chloride (9.74 g crude weight) and 4-dimethylaminopyridine (308 mg) in methylene chloride (30 ml) and triethylamine (8.8 ml). The reaction was stirred at ambient temperature for 72 hours and then partitioned between methylene chloride and saturated sodium bicarbonate. The organic phase was then washed with brine, dried over magnesium sulphate, filtered and evaporated to dryness affording N-(3-nitrophenyl)-3-dimethylaminobenzamide as a solid (8.64 g, 99.9%); NMR (CDCl₃) 3.02(s, 6H), 6.9(m, 1H), 7.09(s, 1H), 7.25(m,1H), 7.35(t, 1H), 7.53(t, 1H), 7.99(m, 1H), 8.05(broad s, 1H), 8.1(m, 1H), 8.5(m,1H); m/s: M + H⁺ 286.
10% Palladium on carbon (637 mg) was added to a stirred solution of N-(3-nitrophenyl)-3-dimethylaminobenzamide (6.37 g) in methanol (180 ml) under an argon atmosphere. Ammonium formate (14.0 g) was added and the reaction heated to 70° C. for 1 hour. After cooling the reaction was filtered through diatomaceous earth (Celite ®). The filtrate was concentrated under vacuum until crystallisation began, water was added and with s-cratching a solid was achieved. The solid was collected and dried in a vacuum oven for 18 hours to yield the required compound (5.02 g, 88%); NMR (CDCl₃) 3.0(s, 6H), 6.47 (m, 1H), 6.8(s, 1H), 6.87(m, 1H), 7.06(m, 1H), 7.11(m, 1H), 7.3(m, 3H), 7.75(broad s, 1H); m/s: M + H⁺ 256.
b) The product gave the following data NMR: 2.14(s, 3H), 3.99(s, 3H), 4.0(s, 3H), 7.34 (m, 2H), 7.50(broad m, 3H), 7.64(m, 1H), 7.92(m, 3H), 8.33(s, 1H), 8.71(s, 1H), 10.37(s, 1H), 11.53(s, 1H); Mass: M + H⁺ 415.
The N-(3-amino-4-methylphenyl)benzamide used as a starting material was prepared as follows:
Benzoyl chloride (1.9 ml) was added to a stirred mixture of 2,4-diaminotoluene (2 g), triethylamine (5.57 ml) and methylene chloride (80 ml) and the mixture was stirred at ambient temperature for 16 hours. The mixture was washed with a saturated aqueous solution of sodium bicarbonate. The organic phase was dried over magnesium sulphate, filtered and evaporated to dryness. The residue was triturated with a mixture of ethyl acetate and diethyl ether to yield the required compound (1.32 g); NMR: 2.01(s, 3H), 4.8(s, 2H), 6.82(m 2H), 7.11(s, 1H), 7.5(m, 3H), 7.91(m, 2H), 9.86(s, 1H); m/s M + H⁺ 227.
c) The product was purified by column chromatography eluting with 10% methanol in methylene chloride. The resultant product gave the following data: NMR: 4.0(2s, 6H), 7.4(s, 1H), 7.50–7.65 (broad m, 4H), 7.81(m, 1H), 7.98(m, 2H), 8.13(m, 1H), 8.32(s, 1H), 8.79(s, 1H), 10.60(s, 1H), 11.73(s, 1H); Mass: M + H⁺ 435 & 437.
The N-(3-amino-4-chlorophenyl)benzamide used as a starting material was prepared as follows:

-continued

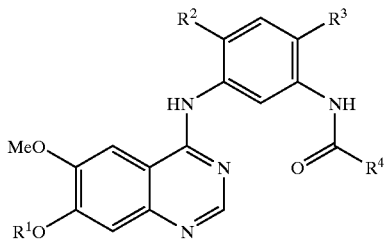

| Ex. No | R¹ | R² | R³ | R⁴ | Method | Note |
|---|---|---|---|---|---|---|

Benzoyl chloride (5.2 ml) was added to a stirred mixture of 2,4-diaminochlorobenzene (6.42 g), triethylamine (12.5 ml) and methylene chloride (100 ml) which had been cooled to 0° C. The mixture was allowed to warm to ambient temperature and was stirred for 16 hours. The mixture was evaporated and the residue was triturated under a saturated aqueous sodium bicarbonate solution. The resultant solid was isolated, washed in turn with water and12 isohexane and dried under vacuum at 55° C. to yield the required compound (10.38 g); NMR 5.32(s, 2H), 6.9(m, 1H), 7.1(d, 1H), 7.37(d, 1H), 7.52(m, 3H), 7.9(d, 2H), 10.05(s, 1H).

d) The product gave the following data: NMR: 2.14(s, 3H), 3.91(2s, 6H), 7.15(s, 1H), 7.29(d, 1H), 7.59(m, 1H), 7.81(m, 2H), 8.00(m, 2H), 8.09(m, 2H), 8.28(s, 1H), 9.39 (s, 1H), 10.46(s, 1H); Mass: M + H⁺ 440.

The N-(3-amino-4-methylphenyl)-4-cyanobenzamide used as a starting material was prepared as follows:

Triethylamine (23 ml) was added to a suspension of 3-nitro-4-methylaniline (0.8 g), 4-cyanobenzoyl chloride (13.1 g), 4-dimethylaminopyridine (0.8 g) in methylene chloride (200 ml) which had been cooled to 0° C. The reaction mixture was allowed to warm to ambient temperature and was stirred for 5 hours. The mixture was partitioned between methylene chloride and 0.5M hydrochloric acid solution. The organic phase was dried over magnesium sulphate, filtered and evaporated to dryness. The residue was triturated under isohexane and the resulting solid was isolated and dried under vacuum at 55° C. to yield N-(4-methyl-3-nitrophenyl)-4-cyanobenzamide (18.3 g); NMR: 2.5(s, 3H), 7.49(d, 1H), 7.96(m, 1H), 8.05(d, 2H), 8.12(d, 2H), 8.51(d, 1H), 10.77(s, 1H).

A solution of tin(II) chloride dihydrate (15.4 g) in concentrated hydrochloric acid (80 ml) was added to a suspension of N-(4-methyl-3-nitrophenyl)-4-cyanobenzamide (6.39 g) in acetic acid (120 ml). The mixture was stirred and heated to reflux for 2 hours. The mixture was allowed to cool to ambient temperature and was basified by the addition of 2M sodium hydroxide solution. The precipitated solid was isolated and dried under vacuum at 55° C. to yield the required compound (5.62 g); NMR: 2.01(s, 3H), 4.85(s, 2H), 6.8(d, 1H), 6.86 (d, 1H), 7.11(s, 1H), 7.96(d, 2H), 8.06(d, 2H), 10.11(s, 1H).

e) The product gave the following data: NMR: 3.99(2s, 6H), 7.41(s, 1H), 7.62(m, 1H), 7.82(m, 1H), 7.95–8.15(m, 6H), 8.35(s, 1H), 8.32(s, 1H), 8.88(s, 1H), 10.9(s, 1H), 11.82 (s, 1H); Mass: M + H⁺ 460 & 462.

The N-(3-amino-4-chlorophenyl)-4-cyanobenzamide used as a starting material was prepared as follows:

4-Cyanobenzoyl chloride (11.92 g) was added slowly to a stirred solution of 4-chloro-3-nitroaniline (10.4 g) in pyridine (20 ml) and the mixture was stirred and heated to 115° C. for 18 hours. The mixture was cooled to ambient temperature and poured into water (150 ml) and stirred for 30 minutes. The resultant precipitate was isolated, washed with water and dried to yield N-[4-chloro-3-nitrophenyl]-4-cyanobenzamide (18 g); m.p. 213° C.; NMR: 7.78(d, 1H), 8.05(m, 3H), 8.1(d, 2H), 8.58(s, 1H), 10.93(s, 1H).

N-[4-chloro-3-nitrophenyl]-4-cyanobenzamide (3.6 g) was added to a stirred suspension of iron powder (10 g) in a mixture of ethanol (130 ml), water (30 ml) and glacial acetic acid (4 ml). The mixture was heated to 75° C. for 1 hour and thereafter, whilst hot, basified by the addition of sodium carbonate. The mixture was filtered and the filtrate was evaporated. The resultant solid was stirred in water for 3 hours. The solid was isolated and dried to yield the required compound (2.7 g); m.p. 237.7° C; NMR: 5.44(s, 2H), 6.98 (m, 1H), 7.21(d, 1H), 7.42(d, 1H), 8.07(d, 2H), 8.14(d, 2H), 10.36(s, 1H).

f) No hydrochloric acid or hydrogen chloride in diethyl ether was used. The product gave the following data: NMR: 2.15(s, 3H), 2.93(s, 6H), 3.99(2s, 6H), 6.91(m, 1H), 7.21 (m, 2H), 7.3(m, 3H), 7.66(m, 1H), 7.88(m, 1H), 8.26(s, 1H), 8.71(s, 1H), 10.23(s, 1H), 11.38 (s, 1H); Mass: M + H⁺ 475.

The N-(3-amino-4-methylphenyl)-3-dimethylaminobenzamide used as a starting material was prepared as follows:

Oxalyl chloride (13.0 ml) was added dropwise to a stirred mixture of 3-dimethylaminobenzoic acid (20.3 g) and N,N-dimethylformamide (a few drops) which had been cooled to 0° C. The mixture was allowed to warm to ambient temperature and was stirred for 4 hours. The resultant mixture was evaporated and the residue was dissolved in methylene chloride (150 ml). 4-Methyl-3-nitroaniline (15.2 g) and triethylamine (27.9 ml) were added in turn and the resultant mixture was stirred at ambient temperature for 16 hours. The reaction mixture was washed in turn with water, with a saturated solution of sodium bicarbonate and with brine, dried over magnesium sulphate, filtered and evaporated to dryness. The residue was triturated under a mixture of ethyl acetate and isohexane. The solid so obtained was filtered off and recrystallized from ethanol to yield N-(4-methyl-3-nitrophenyl)-3-dimethylaminobenzamide (6.1 g); NMR: 2.46(s, 3H), 2.95 (s, 6H), 6.92(d, 1H), 7.22(m, 2H), 7.32(t, 1H), 7.45(d, 1H), 7.97(d, 1H), 8.53(s, 1H), 10.43(s, 1H); m/z M + H⁺ 300.

-continued

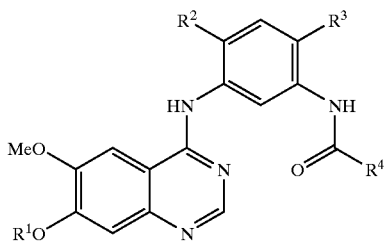

| Ex. No | R¹ | R² | R³ | R⁴ | Method | Note |
|--------|----|----|----|----|--------|------|

N-(4-methyl-3-nitrophenyl)-3-dimethylaminobenzamide (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to yield the required compound (6.89 g); NMR: 2.0 (s, 3H), 2.94(s, 6H), 4.78(s, 2H), 6.82(m, 3H), 7.07(s, 1H), 7.17(m, 2H), 7.25(m, 1H), 9.74(s, 1H); m/z M + H⁺ 270.

g) The product gave the following data: NMR: 3.02(s, 6H), 3.99(2s, 6H), 7.25–7.75 (broad m, 7H). 7.88(m, 1H), 8.11(m, 1H), 8.37(s, 1H), 8.78(s, 1H), 10.7(s, 1H), 11.84(s, 1H); Mass: M + H⁺ 478 & 480.

The N-(3-amino-4-chlorophenyl)-3-dimethylaminobenzamide used as a starting material was prepared as follows:

A solution of 3-dimethylaminobenzoyl chloride hydrochloride (20 g) in methylene chloride (100 ml) was added dropwise over 2 hours to a solution of 4-chloro-3-aminoaniline (14.25 g) and triethylamine (38 ml) in methylene chloride (500 ml), and the reaction stirred at ambient temperature for 18 hours. The precipitated solid was collected to give the title compound (29.7 g, quantitative); NMR: 2.94(s, 3H), 5.28(s, 2H), 6.88(m, 2H), 7.09(d, 1H), 7.16(m, 2H), 7.28(dd, 1H), 7.33(m, 1H), 9.91(s, 1H); m/s 290, 292.

h) Hydrochloric acid (0.1 ml) was used instead of hydrogen chloride in diethyl ether (1.0 ml). Filtered solid was impure and so was purified by column chromatography eluting with 5% methanol in methylene chloride. The product gave the following data: NMR: 3.83(2s, 6H), 3.96(2s, 6H), 7.24(m, 1H), 7.3(m, 2H), 7.54(m, 1H), 7.61(m, 2H), 7.81(m, 1H), 8.02(s, 1H), 8.49(s, 1H), 9.88(s, 1H); Mass: M + H⁺ 475.

The N-(3-amino-4-methylphenyl)-3,4-dimethoxybenzamide used as a starting material was prepared as follows:

A solution of 3,4-dimethoxybenzoyl chloride (13.2 g) in methylene chloride (200 ml) was added dropwise to a stirred mixture of 4-methyl-3-nitroaniline (10 g), pyridine (21.3 ml), 4-dimethylaminopyridine (0.4 g) and methylene chloride (100 ml) and the resultant solution was stirred at ambient temperature for 18 hours. The reaction mixture was washed with 2M hydrochloric acid and water, dried over magnesium sulphate, filtered and evaporated to dryness. The residue was triturated under diethyl ether and the resultant solid was dried under vacuum at 60° C. There was thus obtained N-(4-methyl-3-nitrophenyl)-3,4-dimethoxybenzamide (18.1 g); m.p. 148–149° C.; NMR: (CDCl₃) 2.58(s, 3H), 3.96(s, 6H), 6.92(d, 1H), 7.33(d, 1H), 7.43(m, 1H), 7.51(d, 1H), 7.9(m, 1H), 7.97(broad s, 1H), 8.24(d, 1H).

Ammonium formate (33.9 g) was added to a stirred suspension of N-(4-methyl-3-nitrophenyl)-3,4-dimethoxybezamide (17 g) and 10% palladium-on-carbon (4 g) in ethanol (650 ml) and the mixture was stirred and heated to reflux for 1.5 hours. The reaction mixture was allowed to cool to ambient temperature and filtered. The filtrate was evaporated and the residue was partitioned between methylene chloride and a saturated aqueous sodium bicarbonate solution. The organic phase was washed with water, dried over magnesium sulphate, filtered and evaporated to dryness. The residue was triturated under diethyl ether and the resultant solid was dried under vacuum at 60° C. to yield the required compound(12.6 g); m.p. 143–144° C.; NMR: (CDCl₃) 2.13(s, 3H), 3.65(broad s, 2H), 3.93(s, 6H), 6.73(m, 1H), 6.93(d, 1H), 6.87(m, 1H), 7.0(m, 1H), 7.28(d, 1H), 7.36 (m, 1H), 7.48(d, 1H), 7.7(broad s, 1H).

i) The product gave the following data: NMR: 4.0(s, 6H), 7.37(s, 1H), 7.56(m, 4H), 7.79 (dd, 1H), 7.97(d, 2H), 8.27(s, 1H), 8.82(s, 1H), 10.29(broad s, 1H), 11.58(broad s, 1H); Mass: M + H⁺ 437.

The N-(5-amino-2,4-difluorophenyl)benzamide used as a starting material was prepared as follows:

1,5-Difluoro-2,4-dinitrobenzene (2.48 g) was dissolved in absolute ethanol (150 ml) under an argon atmosphere. 10% palladium on activated carbon (250 mg) was added and the argon atmosphere replaced with hydrogen. The reaction mixture was stirred at ambient temperature until the requisite volume of hydrogen gas was taken up. The catalyst was removed by filtration and the filtrate evaporated to give a black solid. This was dissolved in dry methylene chloride (150 ml) and the solution filtered to remove insoluble material. Triethylamine (1.86 ml) was added followed by benzoyl chloride (0.9 ml) and the resulting mixture was stirred at ambient temperature for 18 hours. The reaction mixture was partitioned between water and methylene chloride, the organic phase was washed with saturated aqueous sodium bicarbonate solution and brine, dried over magnesium sulphate, filtered and evaporated to dryness to give a brown oil. This was purified by eluting through a silica column with 60:40 diethyl ether/isohexane yielding the required compound as a solid(1.06 g, 35%); NMR (CDCl₃) 3.67(broad s, 2H), 6.85(dd, 1H), 7.54(m, 3H), 7.88(d, 2H), 8.01(dd, 1H); m/s: M + H⁺ 249.

-continued

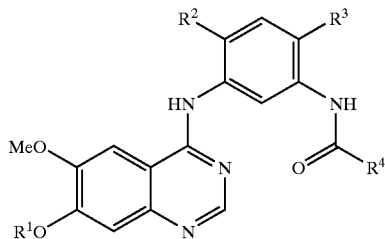

| Ex. No | R¹ | R² | R³ | R⁴ | Method | Note | j) The product was purified by column chromatography, eluting with 97:2:1 methylene chloride/methanol/aqueous ammonia solution. The resultant product gave the following data: NMR: 3.02(s, 6H), 4.05(s, 6H), 6.92(m, 1H), 7.12(m, 2H), 7.32(m, 2H), 7.56(s, 1H), 8.05(s, 1H), 8.73(s, 1H), 9.58(d, 1H); Mass: M + H⁺ 496 & 498.
The N-(5-amino-4-chloro-2-fluorophenyl)-3-dimethylaminobenzamide used as a starting material was prepared as follows:
Pyridine (2.0 ml) was added to a suspension of N-(5-amino-2-chloro-4-fluorophenyl) phthalimide (2.9 g) and 3-dimethylaminobenzoyl chloride hydrochloride (3.06 g) in methylene chloride under an argon atmosphere. The resultant mixture was stirred at ambient temperature for 18 hours. The reaction mixture was diluted with methylene chloride (200 ml) and washed with saturated aqueous copper sulphate solution, water and brine, then dried over magnesium sulphate, filtered and evaporated to dryness. The residue was triturated with warm ethyl acetate, filtered and washed with ethyl acetate and diethyl ether to give N-(5-amino-4-chloro-2-fluorophenyl)phthalimide-3-dimethylaminobenzamide as a solid (2.46 g, 56%); NMR: 2.94(s, 6H), 6.94(m, 1H), 7.28(m, 3H), 7.80–7.92(m, 2H), 7.94(m, 2H), 8.02(m, 2H); m/s: M + H⁺ 438, 440.
Ethanolamine (0.68 ml) was added to a solution of N-(5-amino-4-chloro-2-fluorophenyl) phthalimide-3-dimethylaminobenzamide (2.4 g) in dry methylene chloride (40 ml). The reaction mixture was stirred at ambient temperature for 4 hours. The mixture was diluted with methylene chloride (200 ml) and the resulting solution washed with water and brine, dried over sodium sulphate, filtered and evaporated to dryness to yield the required compound as a solid (1.26 g, 73%); NMR (CDCl₃) 3.02(s, 6H), 3.94(s, 2H), 4.0(broad s, 2H), 6.88(m, 1H), 7.04(m, 1H), 7.07(s, 1H), 7.25(m, 1H), 7.32(t, 1H), 7.98(broad s, 1H), 8.08(d, 1H); m/s: M + H⁺ 308, 310.
k) The free base was generated by partitioning between methylene chloride and saturated sodium bicarbonate, the organic phase was then dried with brine and sodium sulphate, filtered and the filtrate was evaporated to yield a solid. The product gave the following data: NMR: 1.93(m, 2H), 2.12(s, 3H), 2.4(m, 6H), 2.94(s, 6H), 3.56(m, 4H), 3.93(s, 3H), 4.16(m, 2H), 6.9(m, 1H), 7.05–7.35(broad m, 5H), 8.6(m, 1H), 7.77(m, 1H), 7.82(s, 1H), 8.27(s, 1H), 8.27(s, 1H), 9.35(s, 1H), 10.08(s, 1H); Mass: M + H⁺ 570.
l) The product gave the following data: NMR: 3.36(s, 3H), 3.98(s, 6H), 4.05(s, 2H), 7.37 (s, 1H), 7.76(d, 1H), 8.04(d, 1H), 8.23(s, 1H), 8.77(s, 1H), 9.73(s, 1H), 11.57(s, 1H); Mass: M + H⁺ 421 & 423.
The N-(5-amino-4-chloro-2-fluorophenyl)-2-methoxyacetamide used as a starting material was prepared as follows:
Methoxyacetyl chloride (0.65 ml) was added dropwise to a solution of N-(2-chloro-4-fluoro-5-aminophenyl)phthalimide (1.39 g) and triethylamine (1.16 ml) in dry methylene chloride (45 ml) and the resulting mixture was stirred at ambient temperature for 2 hours. The reaction mixture was diluted with methylene chloride and washed with saturated aqueous sodium bicarbonate solution and brine, dried over sodium sulphate, filtered and evaporated to dryness to yield N-[2-chloro-4-fluoro-5-(2-methoxyacetamido)phenyl] phthalimide as a solid (1.72 g, 99%); NMR (CDCl₃): 3.53(s, 3H), 4.04(s, 2H), 7.37(d, 1H), 7.81(m, 2H), 7.98(m, 2H), 8.57(d, 1H), 8.62(broad s, 1H); m/s: [M − H]⁻ 361, 363.
Ethanolamine (0.6 ml) was added to a solution of N-[2-chloro-4-fluoro-5-(2-methoxyacetamido)phenyl]phthalimide (1.408 g) in dry methylene chloride. The reaction mixture was stirred at ambient temperature for 4 hours. The mixture was diluted with methylene chloride (200 ml) and the resulting solution washed with water and brine, dried over sodium sulphate, filtered and evaporated to dryness to yield the required product as a solid (quantitative); NMR (CDCl₃) 3.5(s, 3H), 3.96(broad s, 2H), 4.02(s, 2H), 7.03(d, 1H), 7.91(d, 1H), 8.45(broad s, 1H); m/s: M + H⁺ 233, 235.
m) Prepared using two equivalents of 1M hydrogen chloride solution in diethyl ether. The product was obtained as the dihydrochloride salt and gave the following data: NMR: 2.24 (m, 2H), 3.0(t, 2H), 3.38(s, 3H), 3.97(s, 3H), 4.05(s, 2H), 4.24(t, 2H), 7.37(t, 1H), 7.42(s, 1H), 7.92(dd, 1H), 8.13(dd, 1H), 8.38(s, 1H), 8.44(d, 1H), 8.76(d, 1H), 8.79(s, 1H), 9.6(s, 1H), 11.57(s, 1H); Mass: M + H⁺ 492.5.
The 6-methoxy-4-pentafluorophenoxy-7-(3-pyrid-3-ylpropoxy)quinazoline used as a starting material was prepared as follows:
Under an argon atmosphere, diethyl azodicarboxylate (4.9 ml) was added dropwise to an ice cooled suspension of 7-hydroxy-6-methoxy-4-pentafluorophenoxyquinazoline (7.98 g), 3-(3-pyridyl)-1-propanol (3.16 ml) and triphenylphosphine (8.8 g) in dry methylene chloride (200 ml). The resultant mixture was stirred at ambient temperature for 2 hours. The reaction mixture was evaporated and the residue purified by trituration with diethyl ether, followed by elution through a silica column with 5% methanol in methylene chloride yielding the required compound as a solid (4.96 g, 47%); NMR (CDCl₃) 2.3(m, 2H), 2.92(t, 2H), 4.07(s, 3H), 4.23(t, 2H), 7.24(m, 1H), 7.32(s, 1H), 7.52(s, 1H), 7.56(m, 1H), 8.47(d, 1H), 8.52(s, 1H), 8.58(s, 1H); m/s: M + H⁺ 472.

-continued

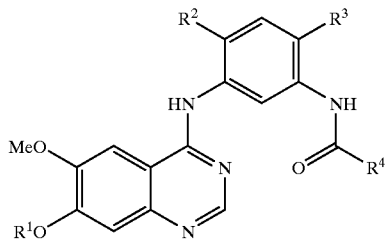

| Ex. No | R¹ | R² | R³ | R⁴ | Method | Note |
|---|---|---|---|---|---|---|

The N-(5-amino-2-fluorophenyl)-2-methoxyacetamide used as a starting material was prepared as follows:
A solution of methoxyacetyl chloride (5.85 ml) in methylene chloride (50 ml) was added dropwise to a solution of 2-fluoro-5-nitroaniline (5.06 g) and triethylamine (8.92 ml) in methylene chloride (150 ml) under an argon atmosphere. The resultant mixture was stirred at ambient temperature for 5 hours, then poured into water and extracted with methylene chloride. The organic phases were washed with brine, dried over magnesium sulphate, filtered and evaporated to dryness to yield N-(2-fluoro-5-nitrophenyl)-2-methoxyacetamide as a solid (7.7 g, 100%); NMR: 3.26(s, 2H), 4.5(s, 3H), 7.57(t, 1H), 8.03(m, 1H), 8.82(m, 1H), 9.83(s, 1H); m/s: M + H⁺ 229.
Iron powder (9.05 g) was added to a solution of N-(2-fluoro-5-nitrophenyl)-2-methoxyacetamide (7.69 g) in a mixture of ethanol (320 ml) and glacial acetic acid (3.2 ml) under an argon atmosphere. The resultant mixture was heated to 90° C. and stirred for 4 hours. Sodium carbonate was added and the mixture stirred for 10 minutes, then filtered warm through diatomaceous earth (Celite ®) and washed with warm ethanol and methylene chloride. The filtrate was evaporated, the residue taken up in water and the resulting solid filtered off, washed with water and diethyl ether. The filtrate was partitioned between ethyl acetate and water, the organic liquors were washed with brine, dried over sodium sulphate, filtered and evaporated to dryness to yield the required compound as a solid (5.38 g, 84%); NMR: (CDCl₃) 3.52(s, 3H), 4.03(s, 2H), 6.33(m, 1H), 6.88(t, 1H), 8.82(m, 1H), 9.83(s, 1H); m/z M + H⁺ 229.
n) Prepared using two equivalents of 1M hydrogen chloride solution in diethyl ether. The product was obtained as the dihydrochloride salt and gave the following data: NMR: 2.32 (m, 2H), 3.1(m, 2H), 3.22–3.53(m, 4H), 3.38(s, 3H), 3.8–4.0(m, 4H), 4.0(s, 3H), 4.06(s, 2H), 4.28(t, 2H), 7.37(t, 1H), 7.41(s, 1H), 7.51(m, 1H), 8.13(dd, 1H), 8.37(s, 1H), 8.79(s, 1H), 9.59(s, 1H), 11.47(s, 1H); Mass: M + H⁺ 500.
o) Prepared using two equivalents of 1M hydrogen chloride solution in diethyl ether. The product was obtained as the dihydrochloride salt and gave the following data: NMR: 3.25–3.45(m, 4H), 3.38(s, 3H), 3.66(t, 2H), 3.95(m, 4H), 4.02(s, 3H), 4.08(s, 2H), 4.68(t, 2H), 7.38(t, 1H), 7.44(s, 1H), 7.52(m, 1H), 8.13(dd, 1H), 8.45(s, 1H), 8.8(s, 1H), 9.6(s, 1H), 11.64(s, 1H); Mass: M + H⁺ 486.5.
The 6-methoxy-7-(2-morpholinoethoxy)-4-pentafluorophenoxyquinazoline used as a starting material was prepared by the reaction of 2-morpholinoethanol and 7-hydroxy-6-methoxy-4-pentafluorophenoxyquinazoline using an analogous procedure to that described in Note m) above for the preparation of 6-methoxy-4-pentafluorophenoxy-7-(3-pyrid-3-ylpropoxy)quinazoline. The required material gave the following data NMR: 2.5(m, 4H), 2.78(t, 2H), 3.58(t, 4H), 3.97(s, 3H), 4.32(t, 2H), 7.48(s, 1H), 7.56(s, 1H), 8.6(s, 1H); Mass: M + H⁺ 472.
p) Prepared using two equivalents of 1M hydrogen chloride solution in diethyl ether. The product was obtained as the dihydrochloride salt and gave the following data: NMR: 1.85 (m, 2H), 2.02(m, 2H), 3.12(m, 2H), 3.38(s, 3H), 3.61(m, 2H), 3.72(m, 2H), ), 4.03(s, 3H), 4.08(s, 2H), 4.6(t, 2H), 7.38(t, 1H), 7.42(s, 1H), 7.52(m, 1H), 8.15(dd, 1H), 8.42(s, 1H), 8.79(s, 1H), 9.59(s, 1H), 11.53(s, 1H); Mass: M + H⁺ 470.5.
The 6-methoxy-7-(2-pyrrolidin-1-ylethoxy)-4-pentafluorophenoxyquinazoline used as a starting material was prepared by the reaction of 2-pyrrolidin-1-ylethanol and 7-hydroxy-6-methoxy-4-pentafluorophenoxyquinazoline using an analogous procedure to that described in Note m) above for the preparation of 6-methoxy-4-pentafluorophenoxy-7-(3-pyrid-3-ylpropoxy)quinazoline. The required material gave the following data: NMR: 1.65(m, 4H), 2.56(m, 4H), 2.88(t, 2H), 3.99(s, 3H), 4.3(t, 2H), 7.45(s, 1H), 7.57(s, 1H), 8.6(s, 1H); Mass: M + H⁺ 456.
q) The product was obtained as the dihydrochloride salt and gave the following data: NMR: 2.16(s, 3H), 3.17(m, 4H), 3.73(m, 4H), 4.0(s, 3H), 4.01(s, 3H), 7.17(d, 1H), 7.37 (m, 4H), 7.46(s, 1H), 7.66(d, 1H), 7.87(s, 1H), 8.33(s, 1H), 8.72(s, 1H), 10.29(broad s, 1H), 11.52(broad s, 1H); Mass: M + H⁺ 500.
The N-(3-amino-4-methylphenyl)-3-morpholinobenzamide used as a starting material was prepared as follows:
A mixture of ethyl 3-bromobenzoate (1.92 ml), morpholine (1.25 ml), 2,2'-bis (diphenylphosphino)-1,1'-binaphthyl (0.336 g), sodium tert-butoxide (1.615 g) and tris (dibenzylideneacetone)dipalladium(0) (0.33 g) and toluene (25 ml) was stirred and heated to 90° C. for 18 hours under argon. The reaction mixture was allowed to cool to ambient temperature and extracted with 1M hydrochloric acid. The aqueous phase was basified with concentrated sodium hydroxide solution and extracted with ethyl acetate. The organic phase was dried over magnesium sulphate, filtered and evaporated to dryness. The residual oil was purified by column chromatography on silica gel using a 47:3 mixture of methylene chloride and methanol as eluent to yield N-(3-morpholinobenzoyl) morpholine (0.45 g).

-continued

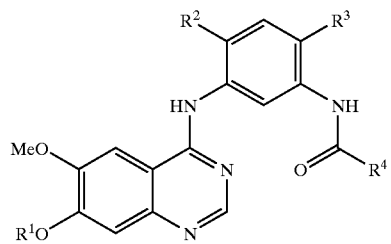

| Ex. No | R¹ | R² | R³ | R⁴ | Method | Note |
|--------|----|----|----|----|--------|------|

A mixture of N-(3-morpholinobenzoyl)morpholine (0.45 g), 5M sodium hydroxide solution (2.5 ml) and butanol (2 ml) was stirred and heated to 115° C. for 18 hours. The mixture was evaporated to dryness and the residue was acidified by the addition of 1M hydrochloric acid solution (12.5 ml). The resultant precipitate was isolated, washed with water and dried to yield 3-morpholinobenzoic acid (0.15 g); NMR: 3.1(t, 4H), 3.73(t, 4H), 7.19(d, 1H), 7.32(d, 1H), 7.38(t, 1H), 7.42(s, 1H).
Oxalyl chloride (0.14 ml) was added to a solution of 3-morpholinobenzoic acid (0.28 g) in methylene chloride (10 ml) which contained N,N-dimethylformamide (2 drops). The reaction mixture was stirred for 18 hours at ambient temperature. The mixture was evaporated and azeotroped with toluene to yield 3-morpholinobenzoyl chloride (0.3 g); M/z M + H⁺ 222.
3-Morpholinobenzoyl chloride (6.22 g) was added to a solution of 4-methyl-3-nitroaniline (4.20 g) and triethylamine (11.0 ml) in methylene chloride (150 ml) at ambient temperature under argon. The reaction mixture was stirred for 18 hours then diluted to 250 ml with methylene chloride. The mixture was washed with water (3 × 150 ml) and saturated sodium bicarbonate solution (2 × 100 ml), dried and evaporated to give a dark brown oil. The oil was triturated with diethyl ether and the solid collected and dried to yield N-(4-methyl-3-nitrophenyl)-3-morpholinobenzamide (1.82 g); NMR: (CDCl₃) 2.53(s, 3H), 3.22 (t, 4H), 3.83(t, 4H), 7.06(dd, 1H), 7.23(d, 1H), 7.37(m, 2H), 7.42(d, 1H), 7.88(dd, 1H), 7.97(s, 1H), 8.21(d, 1H); m/z 340 (MH⁻); m.p. 149–150° C.
10% palladium on carbon (150 mg) was added to a stirred suspension of N-(3-nitro-4-methylphenyl)-3-morpholinobenzamide (1.40 g) in ethanol (100 ml) under argon. The argon atmosphere was replaced with hydrogen and the mixture was stirred at ambient temperature for 4 hours. The catalyst was removed by filtration through diatomaceous earth (Celite ®) and the residue washed with methylene chloride. The filtrate was evaporated to give a solid which was triturated with ethyl acetate to yield N-(3-amino-4-methylphenyl)-3-morpholinobenzamide (1.02 g); NMR: 2.0(s, 3H), 3.19(t, 4H), 3.78(t, 4H), 4.8(s, 2H), 6.8(m, 2H), 7.08(s, 1H), 7.11(d, 1H), 7.34(m, 2H), 7.4(s, 1H), 9.8(s, 1H); m/z 312.
r) The product was purified by column chromatography, eluting with 89:10:1 methylene chloride/methanol/aqueous ammonia solution, relevant fractions concentrated and triturated with methylene chloride. The product gave the following data: NMR: 2.13(s, 3H), 3.51(m, 4H), 3.7(m, 4H), 3.92(2s, 6H), 7.09(m, 1H), 7.15(s, 1H), 7.23(m, 1H) 7.29(m, 1H), 7.59(m, 1H), 7.77(m, 1H), 7.83(s, 1H), 8.26(m, 2H), 9.39(s, 1H) 10.28(s, 1H); Mass: M + H⁺ 501.
The N-(3-amino-4-methylphenyl)-2-morpholinopyridine-4-carboxamide used as a starting material was prepared as follows:
4-Methyl-3-nitroaniline (15.8 g) and 2-chloropyridine-4-carbonyl chloride (20 g) were stirred in methylene chloride (1000 ml) followed by triethylamine (31.8 ml) and stirred at ambient temperature for 72 hours. Reaction was filtered, washed with saturated sodium bicarbonate and methylene chloride and dried in a vacuum oven affording a solid (10.2 g). The original filtrate was washed with saturated sodium bicarbonate. Organic layer was evaporated and then methylene chloride (50 ml) was added and the solid filtered and dried in a vacuum oven to yield 2-chloro-N-(4-methyl-3-nitrophenyl)pyridine-4-carboxamide (8.13 g); NMR: 2.48(s, 3H), 7.51(d, 1H), 7.86(m, 1H), 7.96(m, 2H), 8.49 (m, 1H), 8.64(m, 1H) 10.85(s, 1H); m/s: M + H⁺ 292, 294.
2-Chloro-N-(4-methyl-3-nitrophenyl)pyridine-4-carboxamide (18.33 g) was stirred in morpholine (250 ml) at 100° C. for 18 hours. Reaction was poured into water (250 ml) affording a gummy solid. Methylene chloride (30 ml) was added and stirred for 30 minutes and solid filtered, washed with methylene chloride and dried in a vacuum oven for 18 hours to yield N-(4-methyl-3-nitrophenyl)-2-morpholinopyridine-4-carboxamide the title compound (17.34 g); NMR: 2.48(s, 3H), 3.52(m, 4H), 3.71(m, 4H), 7.1(d, 1H), 7.25 (s, 1H), 7.49(d, 1H), 7.97(m, 1H), 8.29(m, 1H), 8.49(m, 1H), 10.62(s, 1H); m/s: M + H⁺ 343.
Under argon, 5% palladium on carbon (850 mg) was added to N-(4-methyl-3-nitrophenyl)-2-morpholinopyridine-4-carboxamide (8.5 g) in methanol (300 ml). Hydrogen gas was introduced to the reaction via a balloon and stirred at ambient temperature for 18 hours. Methanol (200 ml) was added and the reaction mixture was filtered through celite. The filtrate was evaporated, then stirred in ethyl acetate, filtered again and washed with a small amount of methanol to yield N-(3-amino-4-methylphenyl)-2-morpholinopyridine-4-carboxamide (5.12 g); NMR: 2.01(s, 3H), 3.52(m, 4H), 3.73(m, 4H), 4.83(s, 2H), 6.78(d, 1H), 6.84(d, 1H) 7.04–7.08(m, 2H), 7.20(s, 1H), 8.24(d, 1H), 9.95(s, 1H); m/s: M + H⁺ 313.

Example 46

4-[3-Benzamido-4-fluoroanilino]-6,7-dimethoxyquinoline hydrochloride

Using an analogous procedure to that described in Example 26, 4-chloro-6,7-dimethoxyquinoline was reacted with N-(5-amino-2-fluorophenyl)benzamide to give the title compound; NMR: 3.98 (s, 3H), 4.0 (s, 3H), 6.73 (d, 1H), 7.34 (m, 1H), 7.43 (s, 1H), 7.46 (d, 1H), 7.55 (m, 4H), 7.82 (dd, 1H), 7.98 (d, 2H), 8.13 (s, 1H), 8.37 (d, 1H), 10.32 (broad s, 1H), 10.67 (broad s, 1H); Mass: M+H$^+$ 418.

Example 47

4-[3-Benzamido-4-fluoroanilino]-6,7,8-trimethoxyquinazoline hydrochloride

N-(2-Fluoro-5-aminophenyl)benzamide (276 mg) was added to a suspension of 4-chloro-6,7,8-trimethoxyquinazoline hydrochloride (293 mg) in isopropanol (8 ml) and the resultant mixture stirred and heated to 80° C. for 18 hours. The mixture was cooled to ambient temperature and the precipitated solid was isolated, washed with isopropanol then diethyl ether to yield the title compound as a solid (257 mg, 53%); NMR: 4.0 (s, 3H), 4.01 (s, 3H), 4.07 (s, 3H), 7.42 (t, 1H), 7.52 (m, 2H), 7.62 (m, 2H), 8.0 (m, 3H), 8.35 (s, 1H), 8.72 (s, 1H), 10.28 (s, 1H), 11.84 (broad s, 1H); m/s: M+H$^+$ 449.

Example 48

4-[2-Methyl-5-(3-dimethylaminobenzamido)anilino]-6,7-dimethoxyquinoline

4-Chloro-6,7-dimethoxyquinoline (WO 98/13350 A1) (150 mg) and N-(3-amino-4-methylphenyl)-3-dimethylaminobenzamide (199 mg) were stirred in isopropanol (5 ml) and heated to 85° C. for 18 hours. After cooling to room temperature the precipitated solid was isolated and washed with isohexane. Filtered solid was impure and so was purified by eluting through a silica column with 10% methanol in methylene chloride. The title compound was obtained as a solid (35 mg); NMR: 2.14 (s, 3H), 2.94 (s, 6H), 3.89 (s, 3H), 3.93 (s, 3H), 6.05 (m, 1H), 6.90 (m, 1H), 7.18 (m, 1H), 7.22 (m, 1H), 7.3 (m, 1H), 7.61 (m, 1H), 7.73 (s, 1H), 7.78 (m, 1H), 8.18 (d, 1H), 8.47 (s, 1H), 10.1 (s, 1H); m/s: M+H$^+$ 457.

Example 49

4-[2-Methyl-5-(3,4-dimethoxybenzamido)anilino]-6,7-dimethoxyquinoline hydrochloride Hydrochloric acid (0.15 ml) was added to a mixture of 4-chloro-6,7-dimethoxy quinoline (335 mg) and N-(3-amino-4-methylphenyl)-3,4-dimethoxybenzamide (472 mg) in isopropanol (8 ml) and heated to 85° C. for 18 hours. After cooling to room temperature the precipitated solid was isolated and washed with isohexane to yield the title compound as a solid (180 mg, 24%); NMR: 2.31 (s, 3H), 3.82 (s, 6H), 3.97 (s, 3H), 3.99 (s, 3H), 6.75 (m, 1H), 7.06 (m, 1H), 7.25 (m, 1H), 7.42 (m, 2H), 7.51 (m, 1H), 7.55 (m, 1H), 7.64 (m, 1H), 8.1 (s, 1H), 8.36 (m, 1H), 9.84 (s, 1H), 10.61 (s, 1H); m/s: M+H$^+$ 474.

Example 50

4-[3-(3,4-Dimethoxybenzamido)-4-methylanilino]-6,7-dimethoxyquinoline hydrochloride 4-Chloro-6,7-dimethoxyquinoline (315 mg) and N-(2-methyl-5-aminophenyl)-3,4-dimethoxybenzamide (443 mg) were stirred together in isopropanol (10 ml) and heated to 85° C. for 18 hours. After cooling to room temperature the precipitated solid was isolated and washed with isohexane to yield the title compound as a solid (260 mg, 36%); NMR: 2.32 (s, 3H), 3.82 (s, 6H), 3.97 (s, 3H), 3.99 (s, 3H), 6.75 (m, 1H), 7.07 (m, 1H), 7.25 (m, 1H), 7.46 (m, 2H), 7.51 (m, 1H), 7.58 (m, 1H), 7.64 (m, 1H), 8.1 (s, 1H), 8.36 (m, 1H), 9.85 (s, 1H), 10.62 (s, 1H); m/s: M+H$^+$ 474.

The N-(5-amino-2-methylphenyl)-3,4-dimethoxybenzamide used as a starting material was prepared as follows:—

A solution of 3,4-dimethoxybenzoyl chloride (11.5 g) in methylene chloride (100 ml) was added dropwise to a stirred mixture of 2-methyl-5-nitroaniline (8.74 g), pyridine (18.6 ml) and methylene chloride (200 ml) and the mixture was stirred at ambient temperature for 18 hours. The mixture was washed with 2M hydrochloric acid and with water, dried over magnesium sulphate, filtered and evaporated to dryness. The resultant solid was dried under vacuum at 60° C. to yield N-(2-methyl-5-nitrophenyl)-3,4-dimethoxybenzamide (15.9 g); m.p.>300° C.; NMR: (CDCl$_3$) 2.43 (s, 3H), 3.94 (m, 6H), 6.93 (m, 1H), 7.38 (m, 2H), 7.51 (m, 1H), 7.75 (broad s, 1H), 7.94 (d, 1H), 8.89 (broad m, 1H).

10% Palladium-on-carbon (4 g) was added to a stirred suspension of N-(2-methyl-5-nitrophenyl)-3,4-dimethoxybenzamide (15.9 g) in methanol (1500 ml) and the mixture was stirred under an atmosphere of hydrogen gas. After cessation of hydrogen uptake, the catalyst was removed by filtration and the filtrate was evaporated. The residue was washed with diethyl ether and dried under vacuum at 60° C. to yield the required compound (11.3 g); m.p. 157–158° C.; NMR: (CDCl$_3$) 2.24 (s, 3H), 3.64 (broad s, 2H), 3.95 (m, 6H), 6.44 (m, 1H), 6.93 (d, 1H), 6.98 (d, 1H), 7.38 (m, 1H), 7.54 (m, 2H), 7.6 (broad s, 1H).

Example 51

4-(3-Acetamidoanilino)-6,7-dimethoxyquinoline hydrochloride

The title compound was prepared using the method of Example 50 and the appropriate starting materials; NMR: 2.09 (s, 3H), 3.99 (s, 3H), 4.01 (s, 3H), 6.75 (d, 1H), 7.13 (dt, 1H), 7.48 (m, 3H), 7.89 (s, 1H), 8.15 (s, 1H), 8.35 (d, 1H), 10.32 (br s, 1H), 10.67 (s, br 1H), 14.33 (br s, 1H); m/z 338.

Example 52

6-Acetoxy-7-methoxy-4-[2-methyl-5-(2-morpholinopyridine-4-carboxamido)anilino]quinazoline dihydrochloride A mixture of N-(3-amino-4-methylphenyl)-2-morpholinopyridine-4-carboxamide (178 mg), 6-acetoxy-4-chloro-7-methoxyquinazoline hydrochloride (150 mg) and isopropanol (5 ml) was stirred and heated to 85° C. for 3 hours. The reaction mixture was allowed to cool to ambient temperature and the solid was isolated and washed in turn with isopropanol (5 ml) and isohexane (2×5 ml). There was thus obtained the title compound (249 mg, 80%); NMR: 2.17 (s, 3H), 2.38 (s, 3H), 3.56 (m, 4H), 3.72 (m, 4H), 4.0 (s, 3H), 7.16 (m, 1H), 7.37 (m, 2H), 7.52 (s, 1H), 7.68 (m, 1H), 7.87 (m, 1H), 8.24 (m, 1H), 8.67 (s, 1H), 8.8 (s, 1H), 10.6 (s, 1H), 11.50 (s, 1H); m/s: M+H$^+$ 529.

The 6-acetoxy-4-chloro-7-methoxyquinazoline hydrochloride used as a starting material was prepared as follows:—

A mixture of 6-acetoxy-7-methoxyquinazolin-4-one (International Patent Application WO 96/15118. Example 39 thereof; 4.1 g), thionyl chloride (75 ml) and dimethylformamide (0.2 ml) was stirred and heated to 90° C. for 6 hours. The mixture was evaporated and the residue was azeotroped with toluene. There was thus obtained the required compound as a solid (4.6 g); NMR: 2.3 (s, 3H), 3.94 (s, 3H), 7.4 (s, 1H), 7.83 (s, 1H), 8.68 (s, 1H); M/s: M+H⁺ 253, 255.

Example 53

6-Hydroxy-7-methoxy-4-[2-methyl-5-(2-morpholinopyridine-4-carboxamido)anilino]quinazoline A mixture of 6-acetoxy-7-methoxy-4-[2-methyl-5-(2-morpholinopyridine-4-carboxamido)anilino]quinazoline dihydrochloride (150 mg) and methanolic ammonia (2 ml) was stirred and heated to 50° C. for 48 hours. The mixture was allowed to cool to ambient temperature and the resultant solid was isolated and washed with diethyl ether (10 ml). There was thus obtained the title compound (95 mg, 78%); NMR: 2.12 (s, 3H), 3.51 (m, 4H), 3.7 (m, 4H), 3.97 (s, 3H), 7.09 (m, 1H), 7.12 (s, 1H), 7.23 (m, 2H), 7.57 (m, 1H), 7.69 (s, 1H), 7.72 (m, 1H), 8.23 (s, 1H), 8.26 (m, 1H), 9.17 (s, 1H), 10.28 (s, 1H); m/s: M+H⁺ 487.

Example 54

6-(N,N-Diethylcarbamoylmethoxy)-7-methoxy-4-[2-methyl-5-(2-morpholinopyridine-4-carboxamido)anilino]quinazoline 2-Chloro-N,N-diethylacetamide (0.05 g) was added to a mixture of 6-hydroxy-7-methoxy-4-[2-methyl-5-(2-morpholinopyridine-4-carboxamido)anilino]quinazoline (0.15 g), cesium carbonate (0.3 g) and dimethylacetamide (2 ml) and the reaction mixture was stirred and heated to 100° C. for 18 hours. After cooling to ambient temperature the reaction mixture was partitioned between methylene chloride and water. The organic layer was dried with brine and sodium sulphate, filtered and evaporated. The residual gum was triturated under diethyl ether. There was thus obtained the title compound as a solid (0.04 g, 20%); NMR: 1.05 (t, 3H), 1.4 (t, 3H), 2.13 (s, 3H), 3.35 (m, 4H), 3.51 (m, 4H), 3.7 (m, 4H), 3.95 (s, 3H), 4.91 (s, 2H), 7.11 (m, 1H), 7.18 (s, 1H), 7.24 (s, 1H), 7.29 (m, 1H), 7.6 (m, 1H), 7.77 (m, 2H), 8.26 (m, 2H), 9.3 (broad s, 1H), 10.32 (broad s, 1H); m/s: M+H⁺ 600.

Examples 55–72

Using an analogous procedure to that described in Example 54, 6-hydroxy-7-methoxy-4-[2-methyl-5-(2-morpholinopyridine-4-carboxamido)anilino]quinazoline was reacted with the appropriate alkyl chloride to give the compounds described in the following table. Unless otherwise stated, each appropriate alkyl chloride is either commercially available or is readily prepared by standard methods from known materials.

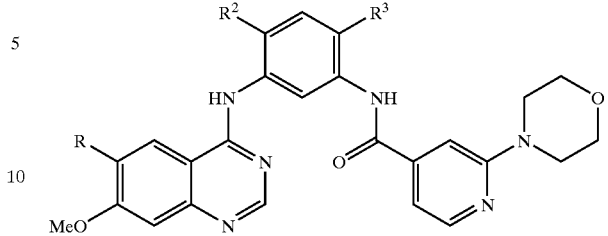

| Ex. No. | R | R² | R³ | Note |
|---|---|---|---|---|
| 55 | N,N-dimethylcarbamoylmethoxy | Me | H | a) |
| 56 | 2-dimethylaminoethoxy | Me | H | b) |
| 57 | 2-diethylaminoethoxy | Me | H | c) |
| 58 | 2-diisopropylaminoethoxy | Me | H | d) |
| 59 | 3-dimethylaminopropoxy | Me | H | e) |
| 60 | 3-diethylaminopropoxy | Me | H | f) |
| 61 | 2-dimethylamino-2-methylpropoxy | Me | H | g) |
| 62 | 2-(pyrrolidin-1-yl)ethoxy | Me | H | h) |
| 63 | 2-piperidinoethoxy | Me | H | i) |
| 64 | 2-morpholinoethoxy | Me | H | j) |
| 65 | 3-(pyrrolidin-1-yl)propoxy | Me | H | k) |
| 66 | 3-morpholinopropoxy | Me | H | l) |
| 67 | 3-(4-methylpiperazin-1-yl)propoxy | Me | H | m) |
| 68 | 2-(N-methylpyrrolidin-2-yl)ethoxy | Me | H | n) |
| 69 | N-methylpiperidin-2-ylmethoxy | Me | H | o) |
| 70 | N-methylpiperidin-3-ylmethoxy | Me | H | p) |
| 71 | N-methyl-5-oxopiperidin-2-ylmethoxy | Me | H | q) |
| 72 | 2-(2-oxoimidazolidin-1-yl)ethoxy | Me | H | r) |

Notes
a) The product gave the following data: NMR: 2.15(s, 3H), 2.92(s, 3H), 3.06(s, 3H), 3.53(m, 4H), 3.7(m, 4H), 3.93(s, 3H), 4.92(s, 2H), 7.1(m, 1H), 7.18(s, 1H), 7.27 (m, 2H), 7.59(m, 1H), 7.75(m, 1H), 8.29(m, 2H), 9.8(broad s, 1H); Mass: M + H⁺ 572.
b) The product gave the following data: Mass: M + H⁺ 558.
c) The product gave the following data: Mass: M + H⁺ 586.
d) The product gave the following data: NMR: 0.95(m, 12H), 2.17(s, 3H), 2.88(s, 2H), 3.04(m, 2H), 3.5(m, 4H), 3.7(m, 4H), 3.93(s, 3H), 4.0(m, 2H), 7.1(m, 1H), 7.17(s, 1H), 7.24(s, 1H), 7.29(m, 1H), 7.59(m, 1H), 7.77 (m, 1H), 7.82(s, 1H), 8.28(m, 2H), 9.42(broad s, 1H), 10.32(broad s, 1H); Mass: M + H⁺ 614.
e) The product gave the following data: Mass: M + H⁺ 572.
f) The product gave the following data: Mass: M + H⁺ 600.
g) 2-Dimethylamino-2-methylpropyl chloride (Chemical Abstracts, volume 58, no. 4477a) was used as the appropriate alkyl chloride. The product gave the following data: Mass: M + H⁺ 586.
The 2-dimethylamino-2-methylpropyl chloride hydrochloride used as a starting material was prepared as follows:
A solution of 2-dimethylamino-2-methylpropan-1-ol (12.78 g) in toluene (100 ml) was dried azeotropically by concentration under reduced pressure to a volume of 50 ml. Thionyl chloride (8.8 ml) was added gradually and the mixture was stirred and heated to 80° C. for 2.5 hours. The mixture was cooled to ambient temperature and evaporated. The solid residue was washed with diethyl ether. There was thus obtained the required compound (10.5 g); NMR: (CDCl₃) 1.61(s, 6H), 2.83(s, 3H), 2.86(s, 3H), 3.86(s, 2H), 12.52(broad s, 1H); Mass: M + H⁺ 136.
h) The product gave the following data: Mass: M + H⁺ 584.
i) The product gave the following data: NMR: 1.3–1.6 (broad m, 6H), 2.15(s, 3H), 2.79(m, 2H), 3.53(m, 4H), 3.7(m, 4H), 3.93(s, 3H), 4.2(t, 2H), 7.1(m, 1H), 7.18(s, 1H), 7.25(s, 1H), 7.29(m, 1H), 7.6(m, 1H), 7.79 (m, 1H), 7.86(m, 1H), 8.27(m, 2H), 9.37(broad s, 1H), 10.28(broad s, 1H); Mass: M + H⁺ 598.
j) The product gave the following data: Mass: M + H⁺ 600.
k) 3-(Pyrrolidin-1-yl)propyl chloride (Chemical Abstracts, volume 128, no. 227441; PCT Patent Application WO 9813354) was used as the appropriate alkyl chloride. The product gave the following data: NMR: 1.68(m, 4H), 1.99(m, 2H), 2.16(s, 3H), 2.48(m, 4H), 2.58(m, 2H), 3.53(m, 4H), 3.72(m, 4H), 3.92(s, 3H), 4.18(m, 2H), 7.09(d, 1H), 7.15(s, 1H), 7.23(s, 1H), 7.28(d, 1H), 7.58(d, 1H), 7.76(s, 1H), 7.82(s, 1H), 8.27(m, 2H), 9.38 (s, 1H), 10.28(s, 1H); Mass: M + H⁺ 598.
l) The product gave the following data: NMR: 2.0 (broad m, 2H), 2.15(s, 3H), 2.4 (m, 2H), 3.53(m, 12H), 3.7(m, 4H), 3.93(s, 3H), 4.15(t, 2H), 7.1 (m, 1H), 7.18(s, 1H), 7.25(s, 1H), 7.29(m, 1H), 7.59(m, 1H), 7.77(m, 1H), 7.83(m, 1H), 8.27(m, 2H), 9.39(broad s, 1H), 10.28(broad s, 1H); Mass: M + H⁺ 614.

-continued

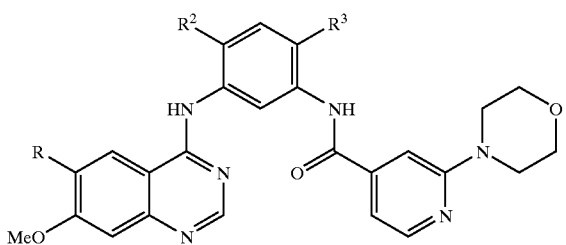

| Ex. No. | R | R² | R³ | Note |
|---|---|---|---|---| m) The product gave the following data: NMR: 1.98(m, 2H), 2.15(2s, 6H), 2.25–2.5(broad m, 10H), 3.52(m, 4H), 3.70(m, 4H), 3.94(s, 3H), 4.15 (broad t, 2H), 7.1(m, 1H), 7.15(s, 1H), 7.23(s, 1H), 7.29(m, 1H), 7.59(m, 1H), 7.78(m, 1H), 7.82(m, 1H), 8.27(m, 2H), 9.38(broad s, 1H), 10.29 (broad s, 1H); Mass: M + H⁺ 627.
n) The product gave the following data: Mass: M + H⁺ 598.
o) N-Methylpiperidin-2-ylmethyl chloride (Chem. Pharm. Bull., 1965, 13(3), 241–247) was used as the appropriate alkyl chloride. The product gave the following data: NMR: 1.6–1.7(m, 6H), 2.17(s, 3H), 2.34(s, 3H), 2.7–2.9(m, 3H), 3.51(m, 4H), 3.7(m, 4H), 3.91(s, 3H), 3.99(m, 1H), 4.22 (m, 1H), 7.1(d, 1H), 7.15(s, 1H), 7.22(s, 1H), 7.28(d, 1H), 7.59(m, 1H), 7.75(s, 1H), 7.83(s, 1H), 8.26(m, 2H), 9.33(d, 1H), 10.28(s, 1H); Mass: M + H⁺ 598.
The 1-methylpiperidin-2-ylmethyl chloride hydrochloride used as a starting material was prepared as follows:
Hydrogen chloride gas was bubbled into a solution of 1-methyl-2-piperidinemethanol (12.9 g) in chloroform (80 ml) until two layers developed. The resultant mixture was heated to reflux and thionyl chloride (29 ml) was added slowly. The mixture was stirred and heated to reflux for a further hour. The mixture was evaporated, ethanol was added and the mixture was re-evaporated. The residue was dissolved in ethanol and the solution was decolourised with charcoal. The clear filtrate was diluted with diethyl ether until turbidity occurred. The required compound (12 g) crystallised from the solution; m.p. 159–162° C.; Mass: M + H⁺ 147.
p) The product gave the following data: Mass: M + H⁺ 598.
q) N-Methyl-5-oxopyrrolidin-2-ylmethyl chloride (Chemical Abstracts, volume 89, no. 163329; J. Org. Chem., 1978, 43, 3750) was used as the appropriate alkyl chloride. The product gave the following data: Mass: M + H⁺ 598.
r) 2-(2-Oxoimidazolidin-1-yl)ethyl chloride (Chemical Abstracts, volume 125, no. 221856; UK Patent Application No. 2295387) was used as the appropriate alkyl chloride. The product gave the following data: Mass: M + H⁺ 599.

Example 73

6-Methoxy-7-(N-methylpiperidin-3-ylmethoxy)-4-[2-methyl-5-(2-morpholinopyridine-4-carboxamido)anilino]quinazoline Using an analogous procedure to that described in Example 26 except that 3 equivalents of the 1M solution of hydrogen chloride in diethyl ether were used, 4-chloro-6-methoxy-7-(N-methylpiperidin-3-ylmethoxy)quinazoline was reacted with N-(3-amino-4-methylphenyl)-2-morpholinopyridine-4-carboxamide. The reaction product was purified by column chromatography on silica using an 89:10:1 mixture of methylene chloride, methanol and a saturated aqueous ammonium hydroxide solution as eluent. There was thus obtained the title compound in 34% yield; NMR: 1.12 (m, 1H), 1.52 (m, 1H), 1.65–2.05 (broad, 3H), 2.15 (s, 3H), 2.2 (s, 3H), 2.7 (m, 2H), 2.90 (m, 2H), 3.53 (m, 4H), 3.73 (m, 4H), 3.95 (s, 3H), 4.04 (d, 2H), 7.1 (m, 1H), 7.16 (s, 1H), 7.24 (m, 1H), 7.31 (m, 1H), 7.59 (m, 1H), 7.78 (m, 1H), 7.84 (s, 1H), 8.27 (m, 2H), 9.4 (s, 1H), 10.3 (s, 1H); m/s: M+H⁺ 598.

The 4-chloro-6-methoxy-7-(N-methylpiperidin-3-ylmethoxy)quinazoline used as a starting material was prepared as follows:—

A mixture of 7-benzyloxy-6-methoxy-3,4-dihydroquinazolin-4-one (20.3 g), thionyl chloride (440 ml) and DMF (1.75 ml) was stirred and heated to reflux for 4 hours. The thionyl chloride was evaporated and the residue was azeotroped with toluene three times to give crude 7-benzyloxy-4-chloro-6-methoxyquinazoline.

A mixture of the crude 7-benzyloxy-4-chloro-6-methoxyquinazoline, 4-chloro-2-fluorophenol (8.8 ml, 83 mmol), potassium carbonate (50 g, 362 mmol) and DMF (500 ml) was stirred and heated to 100° C. for 5 hours. The mixture was allowed to cool to ambient temperature. The reaction mixture was poured into water (2 L) and the resultant mixture was stirred at ambient temperature for a few minutes. The solid so obtained was isolated and washed with water. The resultant solid was dissolved in methylene chloride and filtered through diatomaceous earth. The filtrate was treated with decolourising charcoal, boiled for a few minutes and then filtered through diatomaceous earth. The filtrate was filtered through phase separating paper and evaporated under vacuum to give a solid residue which was triturated under diethyl ether, isolated and dried. There was thus obtained 7-benzyloxy-4-(4-chloro-2-fluorophenoxy)-6-methoxyquinazoline (23.2 g, 76%); NMR: (DMSOd₆) 3.98 (s, 3H), 5.34 (s, 2H), 7.42 (m, 9H), 7.69 (m, 1H), 8.55 (s, 1H).

A mixture of 7-benzyloxy-4-(4-chloro-2-fluorophenoxy)-6-methoxyquinazoline (23 g) and trifluoroacetic acid (150 ml) was stirred and heated to reflux for 3 hours. The reaction mixture was allowed to cool to ambient temperature. Toluene was added and the mixture was evaporated. The residue was triturated under diethyl ether and then under acetone. The precipitate was collected by filtration and dried to give 4-(4-chloro-2-fluorophenoxy)-7-hydroxy-6-methoxyquinazoline (19 g) which was used without further purification; NMR: (DMSOd₆) 3.97 (s, 3H), 7.22 (s, 1H), 7.39 (d, 1H), 7.53 (m, 2H), 7.67 (m, 1H), 8.46 (s, 1H).

A mixture of 4-(4-chloro-2-fluorophenoxy)-7-hydroxy-6-methoxyquinazoline (12.1 g), triphenylphosphine (29.6 g) and methylene chloride (375 ml) was stirred at ambient temperature for 30 minutes. The reaction mixture was cooled in an ice-bath and a solution of N-methylpiperidin-3-ylmethanol (8.25 g) in methylene chloride (75 ml) was added followed by the portionwise addition of diethyl azodicarboxylate (17.7 ml). The reaction mixture was allowed to warm to ambient temperature and was stirred overnight. The mixture was concentrated under vacuum and the residue was purified by column chromatography on silica using initially methylene chloride and then a 93:6:1 mixture of methylene chloride, methanol and an aqueous ammonium hydroxide solution as eluent. The material so obtained was triturated under diethyl ether. There was thus obtained 4-(4-chloro-2-fluorophenoxy)-6-methoxy-7-(N-methylpiperidin-3-ylmethoxy)quinazoline (8.7 g, 53%); NMR: (DMSOd₆) 1.11 (m, 1H), 1.5 (m, 1H), 1.58–1.98 (m, 4H), 2.09 (m, 1H), 2.15 (s, 3H), 2.62 (d, 1H), 2.81 (d, 1H), 3.95 (s, 3H), 4.09 (d, 2H), 7.39 (m, 2H), 7.55 (m, 2H), 7.67 (d, 1H), 8.53 (s, 1H); Mass: M+H⁺ 432.

4-(4-Chloro-2-fluorophenoxy)-6-methoxy-7-(N-methylpiperidin-3-ylmethoxy)quinazoline (8.7 g, 20 mmol) was dissolved in 2M aqueous hydrochloric acid (150 ml) and the mixture was stirred and heated to reflux for 1.5 hours. The reaction mixture was concentrated by evaporation under vacuum and the residue was basified to pH9 by the addition of saturated aqueous ammonium hydroxide solution. The aqueous layer was extracted with methylene chloride (4×400 ml). The combined organic extracts were filtered through phase-separating paper and evaporated. The solid so obtained was triturated under diethyl ether to give 6-methoxy-7-(N-methylpiperidin-3-ylmethoxy)-3,4-dihydroquinazolin-4-one (4.05 g, 66%) as a white solid; NMR: (DMSOd$_6$) 1.05 (m, 1H), 1.40–1.95 (m, 5H), 2.02 (m, 1H), 2.14 (s, 3H), 2.59 (d, 1H), 2.78 (d, 1H), 3.85 (s, 3H), 3.95 (d, 2H), 7.09 (s, 1H), 7.42 (s, 1H), 7.95 (s, 1H), 12.0 (s, 1H); Mass: M+H$^+$ 304.

A mixture of 6-methoxy-7-(N-methylpiperidin-3-ylmethoxy)-3,4-dihydroquinazolin-4-one (2.72 g, 8.9 mmol), thionyl chloride (90 ml) and DMF (0.5 ml) was stirred and heated to reflux for 45 minutes. The mixture was evaporated and the residue was azeotroped with toluene. The residue was taken up in water and basified to pH8 by the addition of a saturated aqueous sodium hydrogen carbonate solution. The aqueous layer was extracted with ethyl acetate (4×400 ml). The combined organic extracts were washed in turn with a saturated aqueous sodium hydrogen carbonate solution, water and brine, dried (MgSO$_4$) and evaporated. The residue was dried overnight at 40° C. under vacuum to give 4-chloro-6-methoxy-7-(N-methylpiperidin-3-ylmethoxy)quinazoline (2.62 g, 91%) as a solid; NMR: (DMSOd$_6$) 1.1 (m, 1H), 1.42–1.96 (m, 5H), 2.09 (m, 1H), 2.15 (s, 3H), 2.6 (d, 1H), 2.8 (d, 1H), 3.98 (s, 3H), 4.1 (d, 2H), 7.35 (s, 1H), 7.42 (s, 1H), 8.84 (s, 1H); Mass: M+H$^+$ 322.

Example 74

4-[5-(4-Cyanobenzamido)-2-methylanilino]-6-methoxy-7-(3-morpholinopropoxy)quinazoline Using an analogous procedure to that described in Example 26, 4-chloro-6-methoxy-7-(3-morpholinopropoxy)quinazoline was reacted with N-(3-amino-4-methylphenyl)-4-cyanobenzamide to give the title compound in 52% yield; NMR: 2.15 (s, 3H), 2.3 (m, 2H), 3.0–4.1 (broad m, 10H), 3.95 (s, 3H), 4.3 (m, 2H), 7.35 (m, 2H), 7.65 (m, 1H), 7.88 (m, 1H), 8.02 (m, 2H), 8.14 (m, 3H), 8.53 (s, 1H), 10.65 (s, 1H), 12.1 (s, 1H); m/s: M+H$^+$ 553.

The 4-chloro-6-methoxy-7-(3-morpholinopropoxy)quinazoline used as a starting material was prepared as follows:—

Sodium hydride (60% dispersion in oil, 0.53 g) was added to a solution of 7-benzyloxy-6-methoxy-4-quinazalone (3.0 g) in dry dimethylformamide (25 ml)and stirred under vacuum for 1 hour. Chloromethyl pivalate (1.96 ml) was added under argon dropwise over 10 minutes and reaction allowed to stir at ambient temperature for 48 hours. Ethyl acetate (25 ml) was added and whole reaction mixture was poured into water. 2M Hydrochloric acid (1.0 ml) was added followed by more ethyl acetate (40 ml) and the reaction was stirred vigorously for 0.5 hour. The resulting solid was filtered, washed with diethyl ether and dried under vacuum for 18 hours. (3.16 g). The filtrate was extracted with ethyl acetate (3×75 ml). The organic phases were combined and washed with water and then brine, dried over magnesium sulphate, filtered and evaporated to dryness. The residue was triturated with diethyl ether. There was thus obtained 7-benzyloxy-6-methoxy-3-pivaloyloxymethyl-3,4-dihydroquinazolin-4-one as a solid (1.01 g; overall yield:—4.17 g, 99%); NMR: 1.11 (s, 9H), 3.91 (s, 3H), 5.27 (s, 2H), 5.91 (s, 2H), 7.24 (s, 1H), 7.43 (m, 6H), 8.34 (s, 1H); m/s: M+H$^+$ 397.

10% palladium on carbon (420 mg) was added to a solution of 7-benzyloxy-6-methoxy-3-pivaloyloxymethyl-3,4-dihydroquinazolin-4-one (4.17 g) in dimethylformamide (30 ml), methanol (30 ml), ethyl acetate (150 ml) and acetic acid (0.42 ml). Hydrogen gas was bubbled into the reaction and it was then stirred at ambient temperature for 18 hours. Reaction was poured through diatomaceous earth (Celite®) and the filtrate was evaporated to dryness and then triturated with diethyl ether and dried to yield 7-hydroxy-6-methoxy-3-pivaloyloxymethyl-3,4-dihydroquinazolin-4-one as a solid, (2.51 g, 78%). NMR: 1.10 (s, 9H), 3.88 (s, 3H), 5.86 (s, 2H), 6.96 (s, 1H), 7.46 (s, 1H), 8.29 (s, 1H); m/s: M+H$^+$ 307.

Potassium carbonate (4.51 g) was added to 7-hydroxy-6-methoxy-3-pivaloyloxymethyl-3,4-dihydroquinazolin-4-one (2.0 g) in dimethylformamide (50 ml) followed by 3-morpholinopropyl chloride (1.3 g) and the reaction was stirred at 100° C. for 6 hours. After cooling the solid was removed by filtration and the filtrate was evaporated and was purified by eluting through a silica column with 10% methanol in methylene chloride to yield 6-methoxy-7-(3-morpholinopropoxy)-3-pivaloyloxymethyl-3,4-dihydroquinazolin-4-one as a solid (1.85 g, 65%); NMR: 1.1 (s, 9H), 1.9 (m, 2H), 2.4 (broad m, 6H), 3.55 (m, 4H), 3.88 (s, 3H), 4.16 (m, 2H), 5.89 (s, 2H), 7.13 (s, 1H), 7.47 (s, 1H), 8.32 (s, 1H); m/s: M+H$^+$ 434.

6-Methoxy-7-(3-morpholinopropoxy)-3-pivaloyloxymethyl-3,4-dihydroquinazolin-4-one (1.85 g) was stirred in methylene chloride (20 ml) and methanol (20 ml) and methanolic ammonia (2M, 100 ml) was added. The reaction was stirred at ambient temperature for 48 hours, evaporated to dryness, and then stirred in diethyl ether for 1 hour. The reaction mixture was filtered affording 6-methoxy-7-(3-morpholinopropoxy)-3,4-dihydroquinazolin-4-one as a solid, (1.22 g, 90%); NMR: 1.9 (m, 2H), 2.4 (broad m, 6H), 3.55 (m, 4H), 3.88 (s, 3H), 4.12 (m, 2H), 7.1 (s, 1H), 7.41 (s, 1H), 7.94 (s, 1H); m/s: M+H$^+$ 320.

6-Methoxy-7-(3-morpholinopropoxy)-3,4-dihydroquinazolin-4-one (1.22 g) was stirred in thionyl chloride (10 ml) with dimethylformamide (0.1 ml) at 85° C. for 1 hour. The reaction was evaporated to dryness, and then azeotroped with toluene. The residue was partitioned between methylene chloride and saturated sodium bicarbonate. The organic phase was separated and evaporated to dryness. The saturated sodium bicarbonate phase was basified with 2M sodium hydroxide and was extracted with methylene chloride. The two organic phases were combined and dried over sodium sulphate, filtered and the filtrate evaporated to dryness. This residue was purified by eluting through a silica column with 5% methanol in methylene chloride to yield 4-chloro-6-methoxy-7-(3-morpholinopropoxy)quinazoline as a solid, (0.5 g, 39%); NMR: 1.95 (m, 2H), 2.4 (broad m, 6H), 3.55 (m, 4H), 3.98 (s, 3H), 4.26 (t, 2H), 7.36 (s, 1H), 7.41 (s, 1H), 8.83 (s, 1H); m/s: M+H$^+$ 338, 340.

Example 75

6-Methoxy-4-[2-methyl-5-(2-morpholinopyridine-4-carboxamido)anilino]-7-(3-morpholinopropoxy)quinazoline Using an analogous procedure to that described in Example 26, 4-chloro-6-methoxy-7-(3-morpholinopropoxy)quinazoline was reacted with N-(3-amino-4-methylphenyl)-2-morpholinopyridine-4-carboxamide to give the title compound in 58% yield; NMR: 1.96 (m, 2H), 2.13 (s, 3H), 3.29 (m, 4H), 3.5 (m, 4H), 3.59 (m, 4H), 3.69 (m, 4H), 3.92 (s, 3H), 4.18 (m, 2H), 7.08 (m, 1H), 7.13 (s, 1H), 7.22 (s, 1H), 7.28 (m, 1H), 7.58 (m, 1H), 7.75 (m, 1H), 7.81 (s, 1H), 8.27 (m, 2H), 9.39 (s, 1H), 10.29 (s, 1H); M/s: M+H$^+$ 614.

Example 76

7-Fluoro-4-[2-methyl-5-(2-morpholinopyridine-4-carboxamido)anilino]quinazoline dihydrochloride Using an analogous procedure to that described in Example 26 except that 2 equivalents of the 1M solution of hydrogen chloride in diethyl ether were used, 4-chloro-7-chloroquinazoline (Chemical Abstracts, volume 122, no. 31545; European Patent Application No. 0602851) was reacted with N-(3-amino-4-methylphenyl)-2-morpholinopyridine-4-carboxamide. After cooling the reaction mixture to room temperature, the precipitated solid was isolated and washed in turn with isohexane and diethyl ether to yield the title compound in 41% yield; m/s: M+H$^+$ 459.

Example 77

6-Methoxy-7-(3-methylsulphonylpropoxy)-4-[2-methyl-5-(2-morpholinopyridine-4-carboxamido)anilino]quinazoline A mixture of 7-hydroxy-6-methoxy-4-[2-methyl-5-(2-morpholinopyridine-4-carboxamido)anilino]quinazoline (250 mg), 3-methylsulphonylpropyl 4-toluenesulphonate (150 mg), cesium carbonate (501 mg) and N,N-dimethylacetamide (5 ml) was stirred and heated to 100° C. for 1 hour. After cooling the reaction mixture to ambient temperature, water was added and the precipitated solid was isolated and dried under vacuum. The material so obtained was purified by column chromatography on silica using a 10:1 mixture of methylene chloride and methanol as eluent. There was thus obtained the title compound as a solid (38 mg); NMR: 2.14 (s, 3H), 2.13 (m, 2H), 3.02 (s, 3H), 3.24 (m, 2H), 3.49 (m, 4H), 3.68 (m, 4H), 3.93 (s, 3H), 4.29 (t, 2H), 7.08 (d, 1H), 7.16 (s, 1H), 7.21 (s, 1H), 7.27 (d, 1H), 7.58 (d, 1H), 7.76 (s, 1H), 7.83 (s, 1H), 8.25 (d, 1H), 8.27 (s, 1H), 9.4 (s, 1H), 10.28 (s, 1H); m/s: M+H$^+$ 607.

The 7-hydroxy-6-methoxy-4-[2-methyl-5-(2-morpholinopyridine-4-carboxamido)anilino]quinazoline used as a starting material was prepared as follows:—

A mixture of 7-benzyloxy-4-chloro-6-methoxyquinazoline hydrochloride (2.95 g), N-(3-amino-4-methylphenyl)-2-morpholinopyridine-4-carboxamide (2.73 g) and isopropanol (60 ml) was stirred and heated to 90° C. for 3 hours. The reaction mixture was cooled to ambient temperature and the precipitated solid was isolated and, washed in turn with isopropanol and isohexane. There was thus obtained 7-benzyloxy-6-methoxy-4-[2-methyl-5-(2-morpholinopyridine-4-carboxamido)anilino]quinazoline dihydrochloride as a solid which was used in the next reaction without further purification; NMR: 2.17 (s, 3H), 3.65 (m 4H), 3.74 (m, 4H), 4.01 (s, 3H), 5.33 (s, 2H), 7.2 (d, 1H), 7.35–7.53 (m, 7H), 7.61 (s, 1H), 7.71 (d, 1H), 7.87 (s, 1H), 8.19 (d, 1H), 8.38 (s, 1H), 8.69 (s, 1H), 10.81 (s, 1H), 11.61 (s, 1H); m/s: M+H$^+$ 577.

A mixture of 7-benzyloxy-6-methoxy-4-[2-methyl-5-(2-morpholinopyridine-4-carboxamido)anilino]quinazoline dihydrochloride (4.45 g) and trifluoroacetic acid (20 ml) was stirred and heated to reflux for 90 minutes. The mixture was cooled to ambient temperature and evaporated. A mixture of a dilute aqueous sodium bicarbonate solution and methylene chloride was added to the residue and the resultant mixture was stirred for 30 minutes at ambient temperature. The precipitated solid was collected, washed with water and, dried under vacuum at 60° C. to give 7-hydroxy-6-methoxy-4-[2-methyl-5-(2-morpholinopyridine-4-carboxamido)anilino]quinazoline (3.67 g; NMR: 2.17 (s, 3H), 3.52 (t, 4H), 3.71 (t, 4H), 3.98 (s, 3H), 7.09 (d, 1H), 7.19 (s, 1H), 7.23 (s, 1H), 7.37 (d, 1H), 7.6 (d, 1H), 7.84 (s, 1H), 8.05 (s, 1H), 8.25 (d, 1H), 8.66 (s, 1H), 10.42 (s, 1H), 11.06 (s, 1H); m/s: M+H$^+$ 487.

The 3-methylsulphonylpropyl 4-toluenesulphonate, used as a starting material was prepared as follows:—

A solution of 3-methylthiopropan-1-ol (9.0 g) in methylene chloride (135 ml) was cooled to 5° C. Triethylamine (13.1 ml) was added followed by 4-tosyl chloride (17.73 g). The mixture was stirred for 18 hours. The reaction mixture was washed with a saturated aqueous sodium bicarbonate solution, dried over magnesium sulphate and evaporated. The residue was purified by column chromatography on silica using a 10:1 mixture of isohexane and ethyl acetate as eluent. There was thus obtained 3-methylthiopropyl 4-toluenesulphonate (9.0 g, 45%); NMR: 1.8 (m, 2H), 1.96 (s, 3H), 2.4 (t, 2H), 2.41 (s, 3H), 4.08 (t, 2H), 7.47 (d, 2H), 7.78 (d, 2H); m/s: M+H$^+$ 261.

A solution of potassium peroxymonosulphate (oxone®; 33 g) in water (250 ml) was added to a solution of 3-methylthiopropyl 4-toluenesulphonate (14.29 g) in methanol (1.5 L). The resulting mixture was stirred for 18 hours, filtered and evaporated. The residue was dissolved in ethyl acetate and the solution was washed with brine, dried over magnesium sulphate and vaporated. There was thus obtained 3-methylsulphonylpropyl 4-toluenesulphonate as a solid (10.22 g, 64%); NMR: 2.01 (m, 2H), 2.43 (s, 3H), 2.95 (s, 3H), 3.1 (t, 2H), 4.13 (t, 2H), 7.47 (d, 2H), 7.78 (d, 2H); m/s: M+NH$_4^+$ 310.

Examples 78–81

Using an analogous procedure to that described in Example 1, the appropriate acyl chloride was reacted with the appropriate aniline to give, unless otherwise stated in the appropriate footnote, the hydrochloride salt of each compound described in the following table.

| Example No. | R$^1$ | R$^3$ | R$^4$ | Note |
|---|---|---|---|---|
| 78 | Me | H | 3-trifluoromethylphenyl | a) |
| 79 | H | H | 2-thienyl | b) |
| 80 | Me | H | cyclopropyl | c) |
| 81 | Me | H | methoxymethyl | d) |

Notes
a) The product gave the following data: NMR: 2.2(s, 3H), 3.98(s, 6H), 7.32(m, 2H), 7.64(d, 1H), 7.77(m, 1H), 7.84(s, 1H), 7.91(d, 1H), 8.08(s, 1H), 8.27(m, 2H), 8.73(s, 1H), 10.32(broad s, 1H); Mass: M + H$^+$ 483.
b) The product gave the following data: NMR: 3.94(s, 3H), 3.97(s, 3H), 7.18(s, 1H), 7.22(m, 1H), 7.34(m, 1H), 7.46(d, 1H), 7.56(d, 1H), 7.85(d, 1H), 7.88(s, 1H), 8.04(d, 1H), 8.2(m, 1H), 8.46(s, 1H), 9.49(s, 1H), 10.25 (s, 1H); Mass: M + H$^+$ 407.
c) The product gave the following data: NMR: 0.76(m, 4H), 2.14(s, 3H), 2.49(m, 1H), 3.97(s, 6H), 7.22(m, 2H), 7.4(d, 1H), 7.65(s, 1H), 7.96(s, 1H), 8.43(s, 1H), 9.92(s, 1H); Mass: M + H$^+$ 379.
d) The product gave the following data: NMR: 2.15(s, 3H), 2.49(m, 2H), 3.39(s, 3H), 3.98(s, 6H), 7.27(d, 1H), 7.29(s, 1H), 7.48(d, 1H), 7.71(s, 1H), 8.04(s, 1H), 8.61(s, 1H), 9.62(s, 1H); Mass: M + H$^+$ 383.

Example 82

4-[4-Fluoro-3-(ethoxycarbonylamino)anilino]-6,7-dimethoxyquinazoline

Ethyl chloroformate (0.058 ml) was added to a suspension of 4-(3-amino-4-fluoroanilino)-6,7-dimethoxyquinazoline (159 mg) and triethylamine (0.14 ml) in dry methylene chloride (3.5 ml) and the resulting mixture was stirred at ambient temperature for 18 hours. Methylene chloride (100 ml) was added and the mixture was washed with water and brine, dried over magnesium sulphate, filtered and evaporated to dryness. The residue was purified by silica column chromatography, eluting with 2% methanol in methylene chloride to yield the title compound as a solid (38 mg, 19%); NMR: 1.23 (t, 3H), 3.91 (s, 3H), 3.94 (s, 3H), 4.12 (m, 2H), 7.16 (s, 1H), 7.21 (m, 1H), 7.57 (m, 1H), 7.83 (s, 1H), 8.0 (m, 1H), 8.42 (s, 1H), 9.28 (s, 1H), 9.49 (s, 1H); m/s: M+H$^+$ 387.

Example 83

4-[5-(4-Cyanobenzamido)anilino]-6-methoxy-7-(3-morpholinopropoxy)quinazoline

Using an analogous procedure to that described in Example 26, 4-chloro-6-methoxy-7-(3-morpholinopropoxy) quinazoline was reacted with N-(3-aminophenyl)-4-cyanobenzamide. The material so obtained was purified by column chromatography eluting with 85:10:5 methylene chloride/methanol/isopropylamine. The material so obtained was triturated under diethyl ether to give the title compound in 48% yield; NMR: 2.1 (m, 2H), 3.35–3.45 (m, 4H), 3.7–3.8 (m, 8H), 3.98 (s, 3H), 4.22 (m, 2H), 7.2 (s, 1 H), 7.38 (m, 1H), 7.51 (m, 1H), 7.58 (m, 1H), 7.93 (s, 1H), 8.04 (d, 2H), 8.13 (d, 2H), 8.31 (s, 1H), 8.46 (s, 1H), 9.59 (s, 1H); Mass: M+H$^+$ 539.

Example 84

6,7-dimethoxy-4-[3-(2-morpholinopyridine-4-carboxamido)anilino]quinazoline

Using an analogous procedure to that described in Example 26, 4-chloro-6,7-dimethoxyquinazoline was reacted with N-(3-aminophenyl)-2-morpholinopyridine-4-carboxamide. The material so obtained was purified by column chromatography eluting with 96:3:1 methylene chloride/methanol/saturated aqueous ammonium hydroxide. The material so obtained was triturated under methylene chloride to give the title compound in 33% yield; NMR: 3.51 (m, 4H), 3.71 (m, 4H), 3.93 (s, 3H), 3.96 (s, 3H), 7.11 (d, 1H), 7.18 (s, 1H), 7.24 (s, 1H), 7.35 (m, 1H), 7.44 (d, 1H), 7.57 (d, 1H), 7.86 (s, 1H), 8.23 (s, 1H), 8.29 (d, 1H), 8.46 (s, 1H), 9.49 (s, 1H), 10.34 (s, 1H); Mass: M+H$^+$ 487.

The N-(3-aminophenyl)-2-morpholinopyridine-4-carboxamide used as a starting material was prepared as follows:—

Triethylamine (6.7 ml) was added to a stirred mixture of 3-nitroaniline (3 g), 2-chloropyridine-4-carbonyl chloride (4.6 g) and methylene chloride (50 ml) and the resultant mixture was stirred at ambient temperature for 40 hours. The mixture was evaporated and the residue was triturated under water. The solid so obtained was isolated, washed with a saturated aqueous sodium bicarbonate solution and dried under vacuum at 55° C. There was thus obtained 2-chloro-N-(3-nitrophenyl)pyridine-4-carboxamide (6.03 g); NMR: (DMSOd$_6$) 7.68 (t, 1H), 7.88 (t, 1H), 7.99 (m, 2H), 8.16 (d, 1H), 8.63 (d, 1H), 8.73 (t, 1H), 10,95 (broad s, 1H); Mass: M+H$^+$ 278.

A mixture of the pyridine-4-carboxamide so produced and morpholine (100 ml) was stirred and heated to 130° C. for 3.5 hours and to 150° C. for 2 hours. The mixture was poured into water (250 ml) and stirred for 10 minutes. The resultant solid was isolated, washed in turn with water and with isohexane and dried under vacuum at 55° C. There was thus obtained N-(3-nitrophenyl)-2-morpholinopyridine-4-carboxamide (6.8 g); NMR: (DMSOd$_6$) 3.52 (t, 4H), 3.71 (t, 4H), 7.12 (d, 1H), 7.25 (s, 1H), 7.66 (t, 1H), 7.97 (d, 1H), 8.15 (d, 1H), 8.29 (d, 1H), 8.73 (t, 1H), 10.72 (broad s, 1H); Mass: M+H$^+$ 329.

A mixture of the material so obtained, 10% palladium-on-carbon catalyst (0.68 g), ammonium formate (13 g) and methanol (150 ml) was stirred and heated to reflux for 2 hours. The reaction mixture was filtered through diatomaceous earth. The filtrate was evaporated and the residue was triturated under water. The resultant solid was isolated, washed in turn with water and with isohexane and dried under vacuum at 55° C. There was thus obtained N-(3-aminophenyl)-2-morpholinopyridine-4-carboxamide (5.38 g); NMR: (DMSOd$_6$) 3.51 (t, 4H), 3.71 (t, 4H), 5.07 (broad s, 2H), 6.33 (d, 1H), 6.81 (d, 1H), 6.95 (t, 1H), 7.05 (m, 2H), 7.2 (s, 1H), 8.24 (d, 1H), 9.96 (broad s, 1H); Mass: M+H$^+$ 299.

Example 85

6-Methoxy-7-[2-(1,2,3-triazol-1-yl)ethoxy]-4-[2-methyl-5-(2-morpholinopyridine-4-carboxamido)anilino]quinazoline A mixture of 7-hydroxy-6-methoxy-4-[2-methyl-5-(2-morpholinopyridine-4-carboxamido)anilino]quinazoline (184 mg), 2-(1,2,3-triazol-1-yl)ethyl 4-toluenesulphonate (101 mg), cesium carbonate (370 mg) and N,N-dimethylacetamide (4 ml) was stirred and heated to 100° C. for 1 hour. After cooling the reaction mixture to ambient temperature, the reaction mixture was partitioned between water and methylene chloride. The organic phase was dried with brine and sodium sulphate and evaporated. The material so obtained was purified by column chromatography on silica using a 10:1 mixture of methylene chloride and methanol as eluent. There was thus obtained the title compound as a solid (47 mg); NMR: 2.14 (s, 3H), 3.51 (t, 4H), 3.72 (t, 4H), 3.91 (s, 3H), 4.59 (t, 2H), 4.87 (t, 2H), 7.09 (d, 1H), 7.2 (s, 1H), 7.22 (d, 1H), 7.27 (d, 1H), 7.58 (m, 1H), 7.74 (s, 2H), 7.83 (s, 1H), 8.18 (s, 1H), 8.24 (d, 1H), 8.26 (s, 1H), 9.39 (s, 1H), 10.28 (s, 1H); m/s: M+H$^+$ 582.

The 2-(1,2,3-triazol-1-yl)ethyl 4-toluenesulphonate used as a starting material was prepared as follows:—

Sodium metal (1.75 g) was added portionwise to anhydrous ethanol (100 ml) and the resultant mixture was stirred at ambient temperature for 30 minutes. 1,2,3-Triazole (5 g) and bromoethanol (5.67 ml) were added in turn and the resultant mixture was stirred and heated to reflux for 5 hours. The mixture was cooled to ambient temperature and filtered. The filtrate was diluted with ethyl acetate and the resultant mixture was filtered. The filtrate was evaporated and the residue was purified by column chromatography on silica using a 3:1 mixture of hexane and ethyl acetate as eluent. There was thus obtained 2-(1,2,3-triazol-1-yl)ethanol (1.95 g); NMR: 3.76 (m, 2H), 4.4 (t, 2H), 4.97 (t, 1H), 7.67 (s, 1H), 8.04 (s, 1H).

Triethylamine (0.68 ml) and 4-toluenesulphonyl chloride (0.19 g) were added in turn to a solution of 2-(1,2,3-triazol-1-yl)ethanol (0.113 g) in methylene chloride (15 ml) which had been cooled to 5° C. The resultant mixture was stirred at ambient temperature for 2 hours. The mixture was evaporated and the residue was purified by column chromatography on silica using increasingly polar mixtures of hexane and ethyl acetate as eluent. There wsa thus obtained the required starting material. (0.85 g); NMR: 2.38 (s, 3H), 4.39 (t, 2H), 4.66 (t, 2H), 7.41 (d, 2H), 7.43 (s, 1H), 7.62 (s, 1H), 7.65 (d, 2H), 8.03 (s, 1H).

Example 86

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection 1 | (50 mg/ml) |
|---|---|
| Compound X | 5.0% w/v |
| 1M Sodium hydroxide solution | 15.0% v/v |
| 0.1M Hydrochloric acid | 4.5% w/v |
| (to adjust pH to 7.6) | |
| Polyethylene glycol 400 | |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|

| -continued | |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:
1. An amide derivative of the Formula (I):

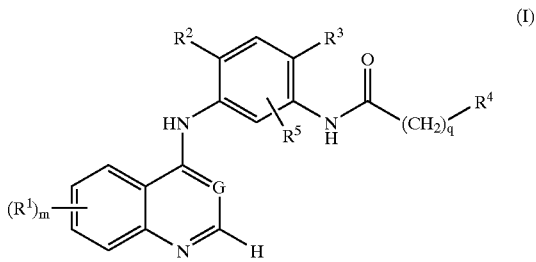

wherein:

G is N or CH;

$R^1$ is hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, or $R^1$ is of the formula (IA):

$$A-(CH_2)_p-B- \qquad (IA)$$

wherein A is halo, hydroxy, $C_{1-6}$alkoxy, $C_{1-6}$alkylS(O)$_n$— (wherein n is 0–2), cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and B is a bond, oxy, imino, N-($C_{1-6}$alkyl)imino or —C(O)NH—, with the proviso that p is 2 or more unless B is a bond or —C(O)NH—, or $R^1$ is of the Formula (IB):

D—E—            (IB)

wherein D is aryl, heteroaryl or heterocyclyl and E is a bond, $C_{1-6}$alkylene, $C_{1-6}$alkyleneoxy, oxy, imino, N-($C_{1-6}$alkyl)imino, $C_{1-6}$alkyleneimino, N-($C_{1-6}$alkyl)-$C_{1-6}$alkyleneimino, $C_{1-6}$alkyleneoxy-$C_{1-6}$alkylene, $C_{1-6}$alkyleneimino-$C_{1-6}$alkylene, N-($C_{1-6}$alkyl)-$C_{1-6}$alkyleneimino-$C_{1-6}$alkylene, —C(O)NH—, —$SO_2$NH—, —$NHSO_2$— or $C_{2-6}$alkanoylimino, and any aryl, heteroaryl or heterocyclyl group in a $R^1$ group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-($C_{1-6}$alkyl)$_2$carbamoyl, $C_{2-6}$alkanoyl, amino, N-$C_{1-6}$alkylamino and N,N-($C_{1-6}$alkyl)$_2$amino, and any heterocyclyl group in a $R^1$ group may be optionally substituted with one or two oxo or thioxo substituents, and any of the $R^1$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^2$ is hydrogen, halo, $C_{1-6}$alkyl, $C_{2-6}$alkenyl or $C_{2-6}$alkynyl;

$R^3$ is hydrogen, halo, $C_{1-6}$alkyl, $C_{2-6}$alkenyl or $C_{2-6}$alkynyl;

$R^4$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy$C_{2-6}$alkoxy, amino$C_{2-6}$alkoxy, N-$C_{1-6}$alkylamino$C_{2-6}$alkoxy, N,N-($C_{1-6}$alkyl)$_2$amino$C_{2-6}$alkoxy or $C_{3-7}$cycloalkyl, or $R^4$ is of the Formula (IC):

—K—J            (IC)

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —$SO_2$NH—, —$NHSO_2$— or —NHC(O)—$C_{1-6}$alkylene-, and any aryl, heteroaryl or heterocyclyl group in a $R^4$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O-($C_{1-3}$alkyl)-O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^4$ group may be optionally substituted with one or more groups of the Formula (IA'):

—$B^1$-($CH_2$)$_p$—$A^1$            (IA')

wherein $A^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—;

or any aryl, heteroaryl or heterocyclyl group in a $R^4$ group may be optionally substituted with one or more groups of the Formula (IB'):

—$E^1$—$D^1$            (IB')

wherein $D^1$ is aryl, heteroaryl or heterocyclyl and $E^1$ is, a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$alkylene, —NHC(O)—, —$NHSO_2$—, —$SO_2$NH— or —NHC(O)—$C_{1-6}$alkylene-, and any aryl, heteroaryl or heterocyclyl group in a substituent on $R^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-($C_{1-6}$alkyl)$_2$carbamoyl, $C_{2-6}$alkanoyl, amino, N-$C_{1-6}$alkylamino and N,N-($C_{1-6}$alkyl)$_2$amino, and any $C_{3-7}$cycloalkyl or heterocyclyl group in a $R^4$ group may be optionally substituted with one or two oxo or thioxo substituents, and any of the $R^4$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^5$ is hydrogen, halo, trifluoromethyl, cyano, nitro, amino, hydroxy, $C_{1-6}$alkyl, $C_{2-6}$alkenyl, $C_{2-6}$alkynyl, $C_{1-6}$alkoxy, N-$C_{1-6}$alkylamino or N,N-($C_{1-6}$alkyl)$_2$amino;

m is 1, 2 or 3; and q is 0, 1, 2, 3 or 4;

or a pharmaceutically acceptable salt or an in vivo cleavable ester thereof; with the proviso that:
4-(3-acetamidoanilino)-6,7-dimethoxyquinazoline; and
4-(3-benzamidoanilino)-6,7-dimethoxyquinazoline are excluded.

2. An amide derivative of the Formula (I) according to claim 1 wherein $R^1$ is hydroxy, halo, $C_{1-6}$alkoxy, N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, heterocyclyl$C_{1-6}$alkyl, heterocyclyl$C_{1-6}$alkoxy, heterocyclyloxy, heterocyclyl$C_{1-6}$alkylamino$C_{1-6}$alkyl or heteroaryl$C_{1-6}$alkoxy.

3. An amide derivative of the Formula (I) according to claim 1 wherein $R^2$ is $C_{1-4}$alkyl or halo when $R^3$ is hydrogen.

4. An amide derivative of the Formula (I) according to claim 1 wherein $R^3$ is $C_{1-4}$alkyl or halo when $R^2$ is hydrogen.

5. An amide derivative of the Formula (I) according to claim 1 wherein $R^4$ is hydrogen or $C_{1-6}$alkoxy or $R^4$ is aryl or heteroaryl optionally substituted by one or more groups selected from halo, cyano, $C_{1-6}$alkyl, $C_{1-6}$alkoxy, N,N-($C_{1-6}$alkyl)$_2$amino or heterocyclyl.

6. An amide derivative of the Formula (I) according to claim 1 selected from:—

4-(3-benzamido-4-fluoroanilino)-6,7-dimethoxyquinazoline, 6-(2-diisopropylaminoethoxy)-7-methoxy-4-[2-methyl-5-(2-morpholinopyridine-4-carboxamido)anilino]quinazoline, 6-(2-dimethylaminoethoxy)-7-methoxy-4-[2-methyl-5-(2-morpholinopyridine-4-carboxamido)anilino]quinazoline, 6-(3-pyrrolidin-1-ylpropoxy)-7-methoxy-4-[2-methyl-5-(2-morpholinopyridine-4-carboxamido)anilino]quinazoline and 4-(3-benzamido-4-fluoroanilino)-6,7-dimethoxyquinoline;

or a pharmaceutically acceptable salt or an in vivo cleavable ester thereof.

7. A process for preparing an amide derivative of the Formula (I), or a pharmaceutically acceptable salt or an in vivo cleavable ester thereof, as claimed in claim 1 which comprises:— a) reacting an aniline of the Formula (II):

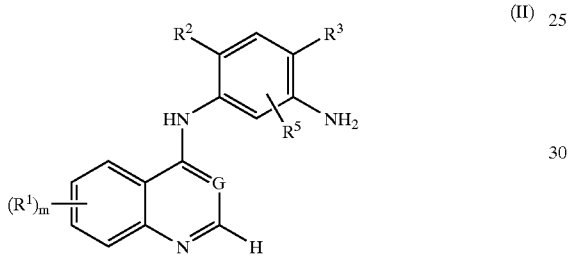

wherein variable groups are as defined in claim 1 and any functional group is protected if necessary, with an acyl compound of the Formula (III):

wherein variable groups are as defined in claim 1, L is a displaceable group and any functional group is protected if necessary;

b) reacting an activated heteroaryl of the Formula (IV):

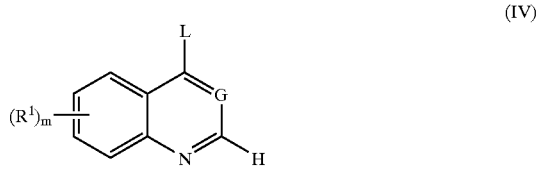

wherein variable groups are as defined in claim 1, L is a displaceable group and any functional group is protected if necessary, with an aniline of the Formula (V):

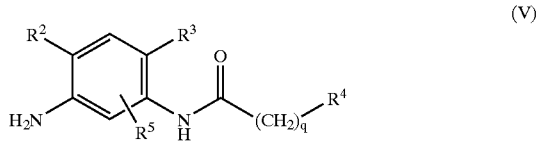

wherein variable groups are as defined in claim 1 and any functional group is protected if necessary; or c) for the preparation of a compound of the Formula (I) wherein $R^1$ or a substituent on $R^4$ is $C_{1-6}$alkoxy or substituted $C_{1-6}$alkoxy, $C_{1-6}$alkylS-, N-$C_{1-6}$alkylamino, N,N-$(C_{1-6}$alkyl$)_2$amino or substituted $C_{1-6}$alkylamino, the alkylation, conveniently in the presence of a suitable base, of an amide derivative of the Formula (I) wherein $R^1$ or a substituent on $R^4$ is hydroxy, mercapto or amino as appropriate; and thereafter if necessary:
  i) converting a compound of the Formula (I) into another compound of the Formula (I);
  ii) removing any protecting groups; and
  iii) forming a pharmaceutically acceptable salt or in vivo cleavable ester.

8. A pharmaceutical composition which comprises an amide derivative of the Formula (I), or a pharmaceutically acceptable salt or an in vivo cleavable ester thereof, as claimed in claim 1 in association with a pharmaceutically acceptable diluent or carrier.

9. A method of treating a disease or medical condition mediated by a cytokine which comprises administering to a warm-blooded animal an effective amount of a compound of Formula (I), or a pharmaceutically-acceptable salt or in vivo cleavable ester thereof, according to claim 1.

* * * * *